(12) United States Patent
Ulman et al.

(10) Patent No.: US 10,744,209 B2
(45) Date of Patent: Aug. 18, 2020

(54) BIODEGRADABLE POLYMERIC NANOPARTICLE CONJUGATES AND USE THEREOF

(71) Applicant: NEW YORK UNIVERSITY, New York, NY (US)

(72) Inventors: Abraham Ulman, Brooklyn, NY (US); Bruce Cronstein, New York, NY (US); Linda Franks, Pelham, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/775,575

(22) PCT Filed: Nov. 11, 2016

(86) PCT No.: PCT/US2016/061542
§ 371 (c)(1),
(2) Date: May 11, 2018

(87) PCT Pub. No.: WO2017/083659
PCT Pub. Date: May 18, 2017

(65) Prior Publication Data
US 2018/0339063 A1     Nov. 29, 2018

Related U.S. Application Data

(60) Provisional application No. 62/254,426, filed on Nov. 12, 2015.

(51) Int. Cl.
| | |
|---|---|
| *A61K 47/69* | (2017.01) |
| *A61K 38/18* | (2006.01) |
| *C07K 14/575* | (2006.01) |
| *A61K 47/59* | (2017.01) |
| *A61P 17/06* | (2006.01) |
| *A61P 19/02* | (2006.01) |
| *A61P 17/02* | (2006.01) |
| *A61K 9/00* | (2006.01) |
| *A61K 31/7076* | (2006.01) |
| *B82Y 5/00* | (2011.01) |
| *A61K 38/00* | (2006.01) |

(52) U.S. Cl.
CPC ........ *A61K 47/6937* (2017.08); *A61K 9/0019* (2013.01); *A61K 31/7076* (2013.01); *A61K 38/18* (2013.01); *A61K 47/593* (2017.08); *A61P 17/02* (2018.01); *A61P 17/06* (2018.01); *A61P 19/02* (2018.01); *C07K 14/575* (2013.01); *A61K 38/00* (2013.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 8,383,093 | B1 * | 2/2013 | Moreadith | A61K 31/381 424/78.3 |
| 8,980,834 | B2 * | 3/2015 | Bar-Or | A61K 45/06 514/16.8 |
| 2006/0246524 | A1 | 11/2006 | Bauer et al. | |
| 2009/0074828 | A1 | 3/2009 | Alexis et al. | |
| 2010/0266491 | A1 | 10/2010 | Farokhzad et al. | |
| 2011/0052715 | A1 | 3/2011 | Davis et al. | |
| 2014/0314864 | A1 * | 10/2014 | Cheng | A61K 9/5031 424/497 |
| 2014/0328854 | A1 | 11/2014 | Maldonado et al. | |
| 2014/0328922 | A1 | 11/2014 | Maldonado | |
| 2014/0356361 | A1 | 12/2014 | Maldonado et al. | |
| 2015/0011496 | A1 | 1/2015 | Cronstein et al. | |

FOREIGN PATENT DOCUMENTS

| | | |
|---|---|---|
| WO | 2013025418 A1 | 2/2013 |
| WO | 2014/179769 A2 | 11/2014 |

OTHER PUBLICATIONS

Viht et al., Bioorganic & Medicinal Chemistry Letters (2003), 13(18), pp. 3035-3039.*
Dworak et al., Polimery (2014), 59(1), pp. 88-94.*
Kazemzadeh-Narbat et al., "Chitosan Nanoparticles as Adenosine Carriers," J. Microencapsul. 8:1-7 (2015).
Zhu et al., "Galactosylated Chitosan Oligosaccharide Nanoparticles for Hepatocellular Carcinoma Cell-Targeted Delivery of Adenosine Triphosphate," Int. J. Mol. Sci. 14:15755-15766 (2013).
Veiseh et al., "Hyaluronan Metabolism in Remodeling Extracellular Matrix: Probes for Imagining and Therapy of Breast Cancer," Integr. Biol. 3:304-315 (2011).
Kokate et al., "Enhancement of Anti-Tumor Effect of Particulate Vaccine Delivery System by 'Bacteriomimetic' CpG Functionalization of Poly-lactic-co-glycolic Acid Nanoparticles," Nanomedicine 10(6):915-929 (2015).
Mittal et al., "Efficient Nanoparticle-Mediated Needle-Free Transcutaneous Vaccination via Hair Follicles Requires Adjuvantation," Nanomedicine 11:147-154 (2015).
Yang et al., "Controlled-Release Levodopa Methyl Ester/Benserazide-Loaded Nanoparticles Ameliorate Levodopa-Induced Dyskinesia in Rats," Int. J. Nanomed. 7:2077-2086 (2012).
Mitra et al., "Enhanced in Vitro Antiproliferative effects of EpCAM Antibody-Functionalized Paclitaxel-Loaded PLGA Nanoparticles in Retinoblastoma Cells," Mol. Vision 17:2724-2737 (2011).
Li et al., "Bypassing Multidrug Resistance in Human Breast Cancer Cells with Lipid/Polymer Particle Assemblies," Int. J. Nanomed. 7:187-197 (2012).
Marin et al., "Critical Evaluation of Biodegradable Polymers Used in Nanodrugs," Int. J. Nanomed. 8:3071-3091 (2013).
Mediero et al., "Adenosine A2a Receptor Ligation Inhibits Osteoclast Formation," Am. J. Pathol. 180(2):775-786 (2012).
Radusky et al., "The Pro-Fibrotic Cytokines IL-33 and IL-13 Modulate Dermal Fibrosis via the A2A Adenosine Receptor," Journal of Investigative Dermatology 132(Supp.1):S10 (2012).
International Search Report and Written Opinion corresponding to PCT/US2016/61542, dated Mar. 13, 2017.
Marin et al., "Critical Evaluation of Biodegradable Polymers Used in Nanodrugs," Int. J. Nanomedicine 8:3071-3091 (2013).

* cited by examiner

*Primary Examiner* — Brian J Davis
(74) *Attorney, Agent, or Firm* — Troutman Pepper Hamilton Sanders LLP (Rochester)

(57) ABSTRACT

The present invention relates to a polymeric nanoparticle conjugate of formula (I). The present invention also relates to pharmaceutical compositions including these polymeric nanoparticle conjugates, and methods of preparation and use thereof.

28 Claims, 14 Drawing Sheets

Cartilage volume:
Nano vehicle 68% of the ctrl
Nano+Ade 89% of the ctrl

Tibia - Nanoparticles

Tibia - NanoADO

BIODEGRADABLE POLYMERIC NANOPARTICLE CONJUGATES AND USE THEREOF

This application is a national stage application under 35 U.S.C. § 371 of PCT Application No. PCT/US2016/061542, filed Nov. 11, 2016, which claims priority benefit of U.S. Provisional Patent Application No. 62/254,426, filed Nov. 12, 2015, which is hereby incorporated by reference in its entirety.

STATEMENT REGARDING FEDERALLY SPONSORED RESEARCH OR DEVELOPMENT

This invention was made with government support under 1UL1TR001445-01 awarded by the National Center for Advancing Translational Sciences (NCATS). The government has certain rights in the invention.

FIELD OF THE INVENTION

The present invention relates to polymeric nanoparticle conjugates, compositions, and methods for making and using them. The polymeric nanoparticle conjugates are useful in the treatment of, for example, wounds and joints to promote surgical healing and for the treatment and/or prevention of arthritis and dermatological conditions.

BACKGROUND OF THE INVENTION

Nano-delivery systems are promising vehicles in drug delivery because they improve solubility of hydrophobic drugs, increase local concentration, provide longer clearance time, increase probability of interactions (e.g. when activation of a receptor is critical), and generally have low toxicity. It has been observed that to avoid clearance by the reticuloendothelial system (RES), the addition of polyethylene glycol (PEG) on the surface of NPs is required (Storm et al., "Surface modification of nanoparticles to oppose uptake by the mononuclear phagocyte system," *Adv. Drug Delivery Rev.* 17:31-48 (1995)). As a consequence of surface PEG molecules, higher maximum tolerated doses (MTD) of nanoparticles (NPs) are realized (Alexis et al., "Nanoparticle technologies for cancer therapy," *Handb. Exp. Pharmacol.* 197:55-86 (2010)). However, certain nano-delivery systems, such as liposomes and dendritic polymers, suffer from deficiencies, such as failure to regulate half-life of a drug once released in vivo.

Osteoarthritis is the most common form of arthritis affecting as many as 29 million people in the United States alone. One in every two people will likely be affected by osteoarthritis. The pathogenesis of osteoarthritis involves low grade inflammation, destruction of articular cartilage and reactive overgrowth of bone in the affected joints. At present therapy is, for the most part palliative, including use of nonsteroidal anti-inflammatory drugs (e.g. ibuprofen), narcotic analgesics, exercise, acupuncture, and injections of anti-inflammatory agents (e.g. glucocorticoids) or other substances (hyaluronic acid) into the joint. Ultimately many patients will undergo replacement of the affected joints.

A very large portion of the heath care budget in the United States relates to the treatment of osteoarthritis (total (direct and indirect) annual costs of osteoarthritis per patient=$5700 FY2000, www.cdc.gov/arthritis/basics/osteoarthritis.htm). Thus, costs, including loss of work, cost of hospitalization for joint replacement and repair surgery and other types of therapy are high and consume a large percentage of the US national health budget. The populations of other developed and developing countries suffer at a similar rate. Moreover, due to increasing obesity and overweight of the population the incidence of knee osteoarthritis and the frequency of total knee replacement is expected to increase dramatically in the near future. At present, short of total joint replacement, there are few long-term effective therapies available. Moreover, although currently available injectable agents (corticosteroids, hyaluronate) provide symptomatic relief none of these agents are restorative. Therefore, improved and more effective treatments of osteoarthritis are required.

The present invention is directed to overcoming these and other deficiencies in the art.

SUMMARY OF THE INVENTION

One aspect of the present invention relates to a polymeric nanoparticle conjugate of formula (I):

$$P{-}[L{-}T]_n \qquad (I),$$

wherein
P is a core polymeric matrix;
L is a surface linker group, wherein the surface linker group is a hydrophilic polymer moiety;
T is a therapeutic agent which can be the same or different at each occurrence, wherein in at least one occurrence T is selected from the group consisting of adenosine, an $A_{2A}$ adenosine receptor agonist, an $A_{2B}$ adenosine receptor agonist, an $A_3$ adenosine receptor agonist, and analogues or derivatives thereof, and wherein T is covalently linked to L; and
n is 1 to 500.

Additional aspects of the present invention include pharmaceutical compositions comprising a pharmaceutically acceptable carrier and polymeric nanoparticle conjugate of the invention and, optionally, one or more additional additive agent(s) as discussed below.

Another aspect of the present invention relates to a method of treating and/or preventing arthritis in a patient in need thereof. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an $A_{2A}$ adenosine receptor agonist, an $A_{2B}$ adenosine receptor agonist, and an $A_3$ adenosine receptor agonist.

Yet another aspect of the present invention relates to a method of treating a wound in a patient in need thereof. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an $A_{2A}$ adenosine receptor agonist, an $A_{2B}$ adenosine receptor agonist, and an $A_3$ adenosine receptor agonist.

A further aspect of the present invention relates to a method of treating and/or preventing a dermatological condition in a patient in need thereof. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an $A_{2A}$ adenosine receptor agonist, an $A_{2B}$ adenosine receptor agonist, and an $A_3$ adenosine receptor agonist.

Another aspect of the present invention relates to method of treating a joint to promote surgical healing. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an $A_{2A}$ adenosine receptor agonist, an $A_{2B}$ adenosine receptor agonist, and an $A_3$ adenosine receptor agonist.

In one particular embodiment, the present invention relates to the preparation of adenosine- or adenosine agonist-functionalized biodegradable nanoparticles (see, e.g., FIGS. 1A-B), and their successful use in activating the adenosine receptor. These biodegradable nanoparticles can regulate fibroblasts, osteoclasts and macrophage cells via adenosine A2A receptors and, likely, A2B receptors. Adenosine A2A receptor agonists have been used for the promotion of wound healing in the skin (see, e.g., Cronstein et al., "The Antiinflammatory Mechanism of Methotrexate. Increased Adenosine Release at Inflamed Sites Diminishes Leukocyte Accumulation in an In Vivo Model of Inflammation," *J. Clin. Invest.*, 92(6):2675-2682 (1993), which is hereby incorporated by reference in its entirety). Stimulation of adenosine receptors on chondrocytes (the cells primarily affected in osteoarthritis) suppresses the effects of inflammation on these cells. Adenosine itself has an extremely short half-life in vivo (<10 seconds), so the effective delivery of adenosine in clinical applications is a significant challenge. When a drug is delivered in a nano-delivery system such as a liposome or the like, once released, the half-life of the drug remains the same. When a drug is encapsulated in a dendritic polymer, its release time might be slower, but the life-time once released is again the same. The present invention overcomes these difficulties and provides nanoparticles with a residence time significantly longer than previous systems. Moreover, as there can be many adenosine or adenosine agonist molecules on each nanoparticle, there is a higher statistical probability for activating a receptor and the possibility that one particle will activate more than one receptor or receptors on adjacent cells.

BRIEF DESCRIPTION OF THE DRAWINGS

FIG. 4B shows a graph of the results. Both concentrations of nanoparticles reduced the number of TRAP-positive cells in as similar way as CGS21680, which is reversed in the presence of the A2AR antagonist.

FIG. 6A shows representative 3D reconstructions of knee joints of wild type (WT) and A2AR KO mice showing bony sclerosis (square) in the subchondral bone in the tibial plateaus in 12-week- and 26-week-old male and female mice. Osteophytes are evident in 26-week-old A2AR KO mice (arrow). FIG. 6B shows representative photographs of the distal femoral condyle from WT and A2AR KO mice at 12, 16, and 26 weeks. Early fibrillation progressing to frank loss of cartilage in the femoral condyles of A2AR KO mice is demonstrated in these photographs.

FIG. 7A shows a reduction of cartilage thickness in tibia and femurs of A2AR KO mice compared to WT mice (10× original magnification, squares shown at higher magnification in FIG. 7B). FIG. 7B illustrates that the articular cartilage of 16- and 26-week-old A2AR KO mice shows, in addition to thinning and fibrillation, cellular changes (40× original magnification).

FIG. 10A is a graph of results demonstrating that adenosine-conjugated nanoparticles inhibit accumulation of mRNA for IL-6 in IL-1B-stimulated primary murine chondrocytes. FIGS. 10B and 10C are graphs of results demonstrating that adenosine-conjugated nanoparticles inhibit IL-1B-stimulated accumulation of mRNA for MMP13 (FIG. 10B) and Col 10a1 (FIG. 10C) via A2B receptors. FIG. 10D is a graph showing experimental results demonstrating that adenosine-conjugated nanoparticles inhibit activation of NF-kB via A2A adenosine receptors.

FIG. 12C is a graph showing cartilage volume in the affected joint as percent of control (i.e., unaffected opposite joint) in rats treated with adenosine-conjugated nanoparticles (89% of control unaffected opposite knee) compared to unconjugated nanoparticles (68% of control).

In FIG. 13, the 5'-OH is shown with both the Fe proton (shown as a sphere), which is H-bond donor, and the two lone pairs (shown as orbitals) which are H-bond receptors. Similarly, in the amine, the two hydrogens (shown as spheres) and electron pair (shown as an orbital) are shown.

DETAILED DESCRIPTION OF THE INVENTION

One aspect of the present invention relates to a polymeric nanoparticle conjugate of formula (I):

 (I), wherein

P is a core polymeric matrix;

L is a surface linker group, wherein the surface linker group is a hydrophilic polymer moiety;

T is a therapeutic agent which can be the same or different at each occurrence, wherein in at least one occurrence T is selected from the group consisting of adenosine, an $A_{2A}$ adenosine receptor agonist, an $A_{2B}$ adenosine receptor agonist, an $A_3$ adenosine receptor agonist, and analogues or derivatives thereof, and wherein T is covalently linked to L; and n is 1 to 500.

Figure 1A:
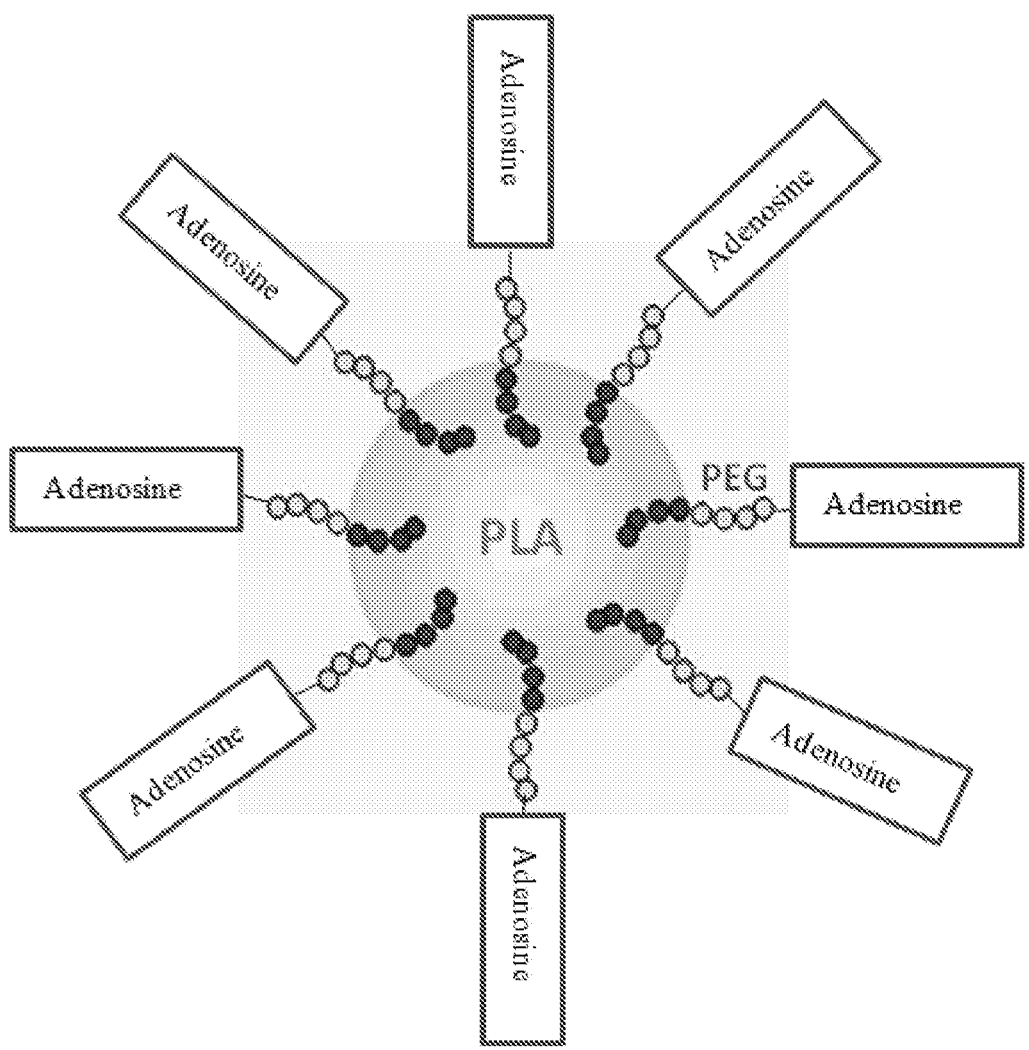
FIGS. 1A and 1B are illustrations showing a poly(lactic acid) (PLA) nanoparticle conjugated with adenosine using a polyethylene glycol (PEG) linker.
Figure 1B:
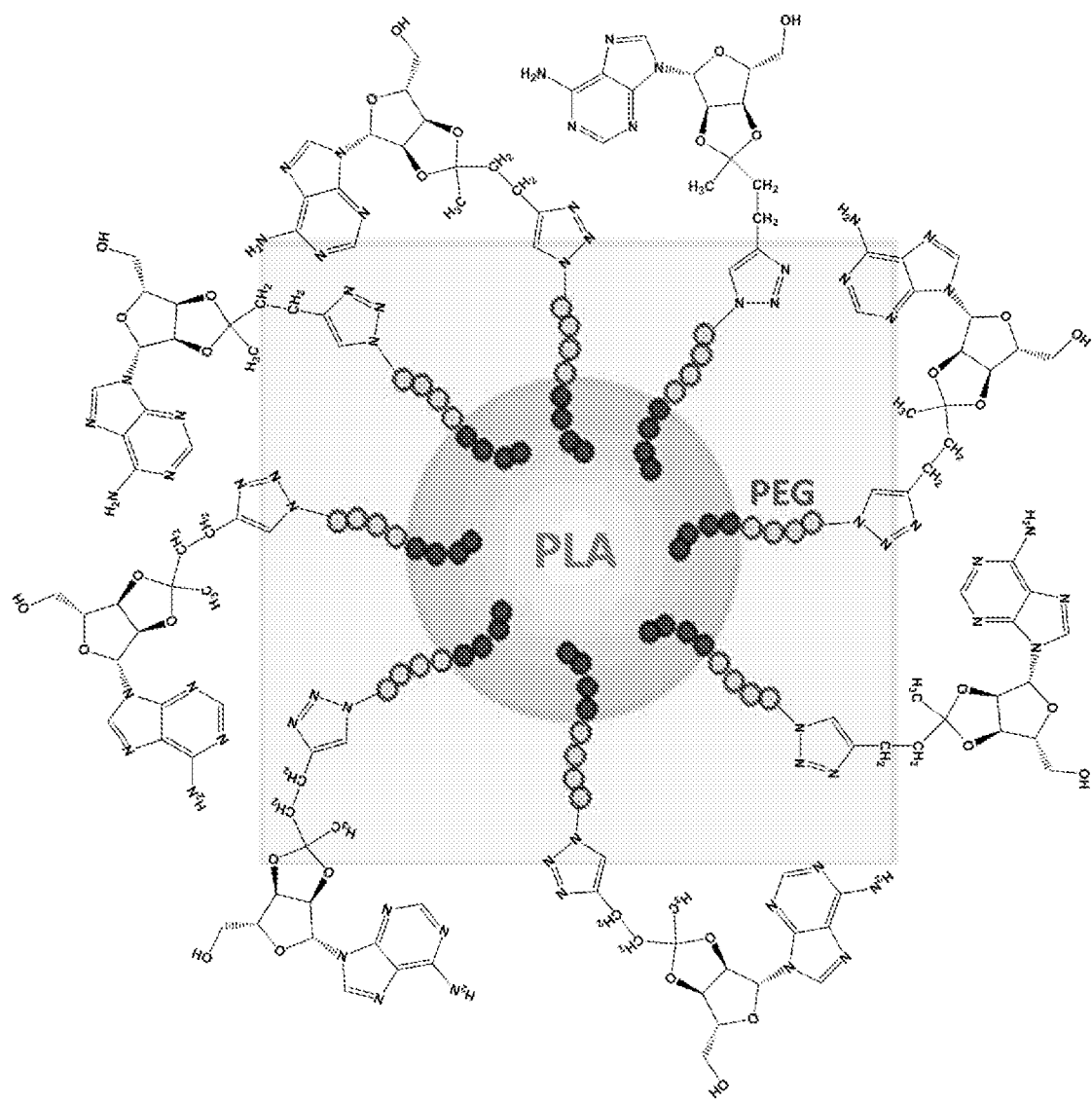

The core polymeric matrix P comprises one or more polymers that associate or assemble to form a polymeric matrix. A wide variety of suitable polymers are described below and methods for forming polymeric matrices therefrom are known in the art. The core polymeric matrix can be a variety of different shapes, including, but not limited to, spheroidal, cuboidal, pyramidal, cylindrical, oval, flat, disc-shaped, and the like. An example of a spheroidal core polymeric matrix is shown in FIGS. 1A-B. In one embodiment, the core polymeric matrix can have a core/shell structure.

In one embodiment, P is biodegradable.

In another embodiment, P is hydrophobic.

In another embodiment, the core polymeric matrix P is synthetic, semisynthetic, or natural, all biodegradable. Polymers may be homopolymers or copolymers comprising two or more monomers. Suitable copolymers can be, for example, block copolymers. Polymers can be linear or branched polymers. The polymers listed herein represent an exemplary, not comprehensive, list of polymers that can be of use in accordance with the present invention. Other suitable polymers are described, for example, in WO 2014/179769, which is hereby incorporated by reference in its entirety.

In yet another embodiment, the core polymeric matrix P comprises polyesters, poly(ester amide)s, polyurethanes, polyanhydrides, polyphosphoesters, poly(ortho esters), poly (alkyl cyanoacrylates), polyether, poly(amino acids), or combinations thereof.

In a further embodiment, P is a polyester selected from the group consisting of poly(glycolic acid), poly(lactic acid), poly(caprolactone), poly(lactic-co-glycolic acid), poly(butylene succinate), poly(trimethylene carbonate), poly(p-dioxanone), poly(buthylene terephthalate), and combinations thereof.

In another embodiment, core polymeric matrix P comprises poly(lactic acid) (PLA), poly(caprolactone) (PCL), or poly(lactic-co-glycolic acid) (PLGA). PLA is suitable for use as a matrix material for polymeric nanoparticle preparation because of its biodegradable and safe properties. As early as the 1970's, PLA products have been approved by the US Food and Drug Administration (FDA) for direct contact with biological fluids.

In another embodiment, core polymeric matrix P comprises Hybrane®S1200 (poly(ester amide)), DegraPol® (polyurethane), poly[(carboxyphenoxy)propane-sebacic acid], poly[bis(hydroxyethyl)terephthalate-ethyl orthophosphorylate/terephthaloyl chloride], poly(ortho esters)I, poly (ortho esters)II, poly(ortho esters)III, poly(ortho esters)IV, poly(butyl cyanoacrylate), poly(ethylene glycol), tyrosine derived polycarbonate, or combinations thereof.

In yet another embodiment, core polymeric matrix P comprises microbial polyesters.

In a further embodiment, the microbial polyester is selected from the group consisting of poly(β-hydroxyalkanoate)s, poly(hydroxybutyrate), and poly(hydroxybuthyrate-co-hydroxyvalerate).

In yet another embodiment, core polymeric matrix P comprises proteins or polysaccharides.

In another embodiment, the core polymeric matrix comprises collagen, albumin, gluten, chitosan, hyaluronate, hyaluronic acid, cellulose, alginate, or starch.

In a further embodiment, the starch is hydroxyethyl starch.

Any suitable hydrophilic linker group L can be used in accordance with the present invention. In one particular embodiment, surface linker group L is selected from the group consisting of polyethylene glycol (PEG) and polypropylene glycol (PPG).

L may be a surface linker group (e.g., PEG) with any suitable molecular weight. L may be a surface linker group (e.g., PEG) with a molecular weight of, for example, 100,000 daltons or less; 20,000 daltons or less; 10,000 daltons or less; 5,000 daltons or less; 3,000 daltons or less; 2,000 daltons or less; 1,000 daltons or less; 500 daltons or less; 400 daltons or less; or 200 daltons or less. L may be a surface linker group with a molecular weight of 400 daltons to 100,000 daltons; 400 daltons to 20,000 daltons; 400 daltons to 10,000 daltons; 400 daltons to 5,000 daltons; 400 daltons to 3,000 daltons; 400 daltons to 2,000 daltons; 400 daltons to 1,000 daltons; 400 daltons to 500 daltons; 500 daltons to 100,000 daltons; 500 daltons to 20,000 daltons; 500 daltons to 10,000 daltons; 500 daltons to 5,000 daltons; 500 daltons to 3,000 daltons; 500 daltons to 2,000 daltons; 500 daltons to 1,000 daltons; 1,000 daltons to 100,000 daltons; 1,000 daltons to 20,000 daltons; 1,000 daltons to 10,000 daltons;

1,000 daltons to 5,000 daltons; 1,000 daltons to 3,000 daltons; 1,000 daltons to 2,000 daltons; 2,000 daltons to 100,000 daltons; 2,000 daltons to 20,000 daltons; 2,000 daltons to 10,000 daltons; 2,000 daltons to 5,000 daltons; 2,000 daltons to 3,000 daltons; 3,000 daltons to 100,000 daltons; 3,000 daltons to 20,000 daltons; 3,000 daltons to 10,000 daltons; 3,000 daltons to 5,000 daltons; 5,000 daltons to 100,000 daltons; 5,000 daltons to 20,000 daltons; 5,000 daltons to 10,000 daltons; 10,000 daltons to 100,000 daltons; 10,000 daltons to 20,000 daltons; or 20,000 daltons to 100,000 daltons. Linker may be a moiety with a molecular weight of at least about 100,000 daltons; 20,000 daltons; 10,000 daltons; 5,000 daltons; 3,000 daltons; 2,000 daltons; 1,000 daltons; 500 daltons; 400 daltons; or 200 daltons. In certain embodiments of the invention polyethylene glycol 2000 (PEG 2000) is used.

In a further embodiment, P comprises poly(lactic acid) (PLA), poly(caprolactone) (PCL), or poly(lactic-co-glycolic acid) (PLGA) and L comprises polyethylene glycol (PEG). In an additional embodiment, P-T comprises a PLA-PEG diblock copolymer.

In another embodiment, at least one therapeutic agent T is adenosine or a derivative or analogue thereof.

In a further embodiment, the at least one therapeutic agent T is an agonist for any of the four known subtypes of adenosine receptors. By "agonist" is meant a substance that binds to a specific receptor and triggers a response in a cell. It mimics the action of an endogenous ligand (such as hormone or neurotransmitter) that binds to the same receptor. A "full agonist" binds (has affinity for) and activates a receptor, displaying full efficacy at that receptor. A "partial agonist" also binds and activates a given receptor, but has only partial efficacy at the receptor relative to a full agonist. A "partial agonist" may also be considered a ligand that displays both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone. A "co-agonist" works with other co-agonists to produce the desired effect together. An "indirect agonist" works by increasing endogenous adenosine levels. Suitable indirect agonists include, for example, adenosine uptake inhibitors. Receptors can be activated by endogenous (such as hormones and neurotransmitters) or exogenous (such as drugs) agonists, resulting in stimulating a biological response. The potency of an agonist is usually defined by its $EC_{50}$ value, which can be calculated by determining the concentration of agonist needed to elicit half of the maximum biological response of the agonist. The lower the $EC_{50}$ value, the greater the potency of the agonist and the lower the concentration of drug that is required to elicit a maximum biological response. Suitable agonists as described herein have $EC_{50}$ values of from about 1 nM to about 1 µM. Unless otherwise stated, the term "agonist" can refer to a full, partial, or co-agonist.

In another embodiment, at least one therapeutic agent T is an alkyne derivative of: adenosine, an A2A adenosine receptor agonist, an A2B adenosine receptor agonist, or an A3 adenosine receptor agonist.

Representative adenosine receptor agonists that can be used in accordance with the present invention include the following:

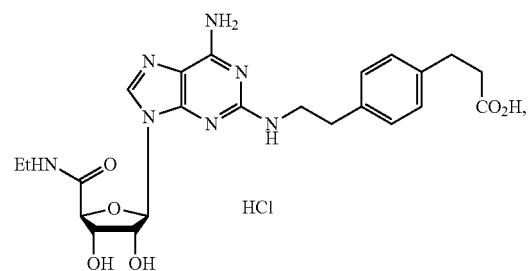

I

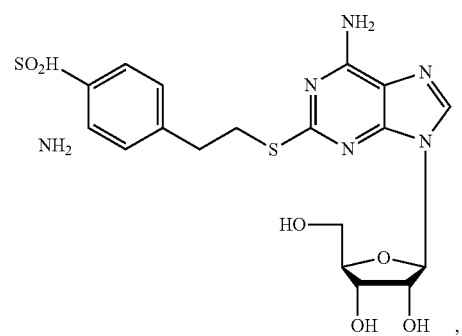

II

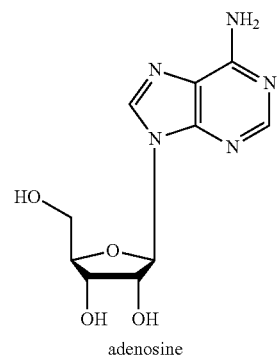

adenosine

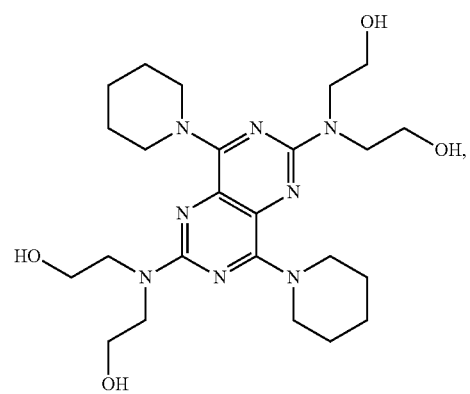

dipyridamole

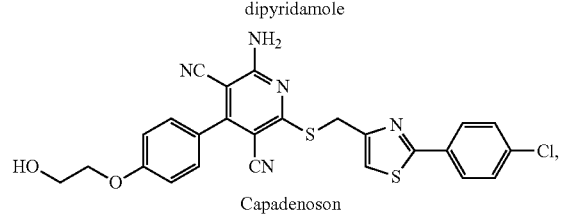

Capadenoson

-continued
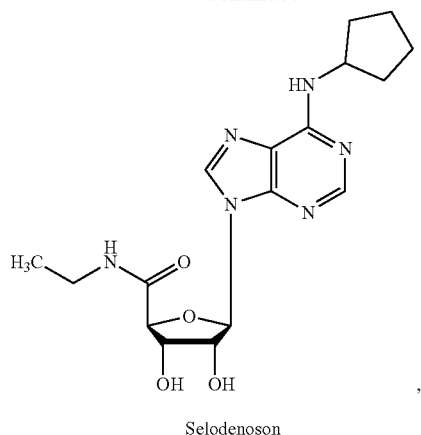
Selodenoson
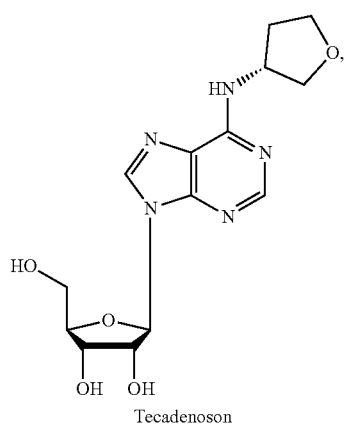
Tecadenoson
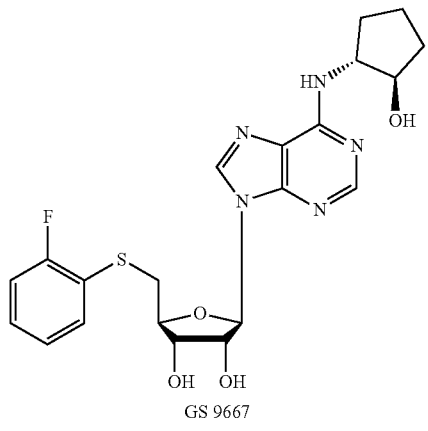
GS 9667
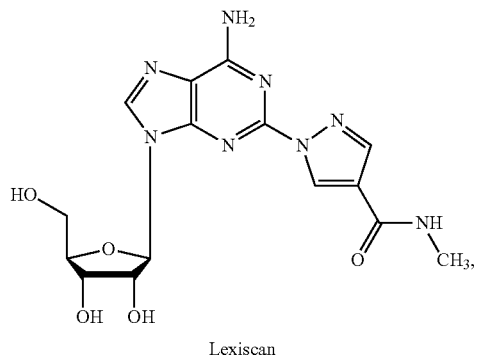
Lexiscan
-continued
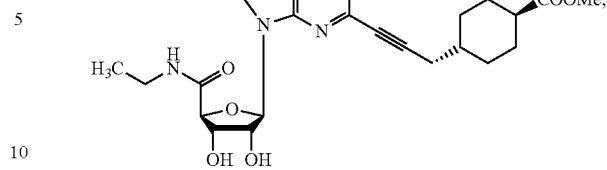
Apadenoson
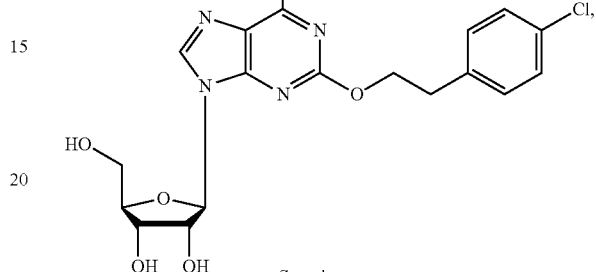
Sonedenoson
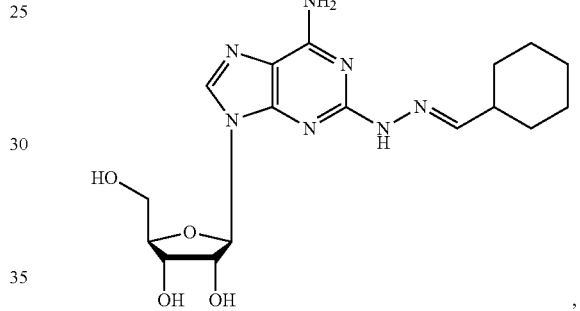
Binodenoson
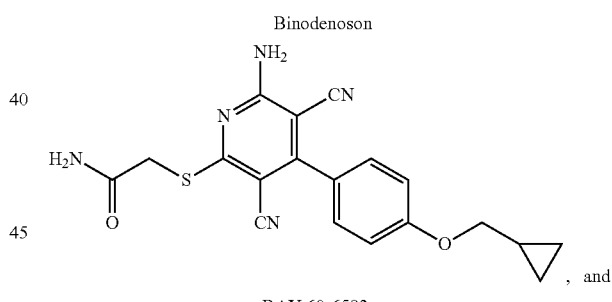
BAY 60-6583
, and
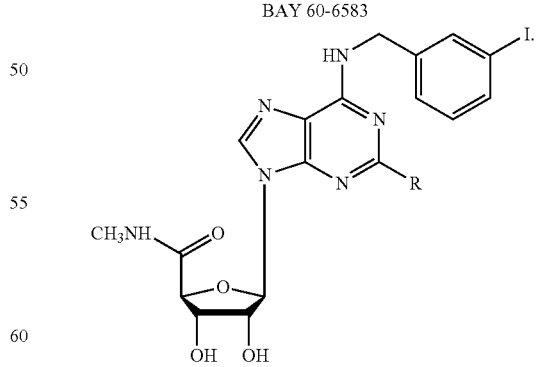
R = H, IB-MECA
R = Cl, Cl-IB-MECA
Molecule I is an A2A adenosine receptor agonist ($K_i$=27 nM), which has affinity for A1 and A3 adenosine receptors but can be also used to distinguish A2A- and A2B-mediated effects. Molecule II is a potent adenosine A2A receptor full agonist. It exhibits subtype selectivity for A2A receptors over A1, A2B and A3 receptors. ($K_i \geq 10\,000$ nM for rat $A_1$, human A2B, and human A3 receptors). The above representative agonists include, for example, indirect agonists (adenosine uptake inhibitors) that work by increasing endogenous adenosine levels.

Figure 2:
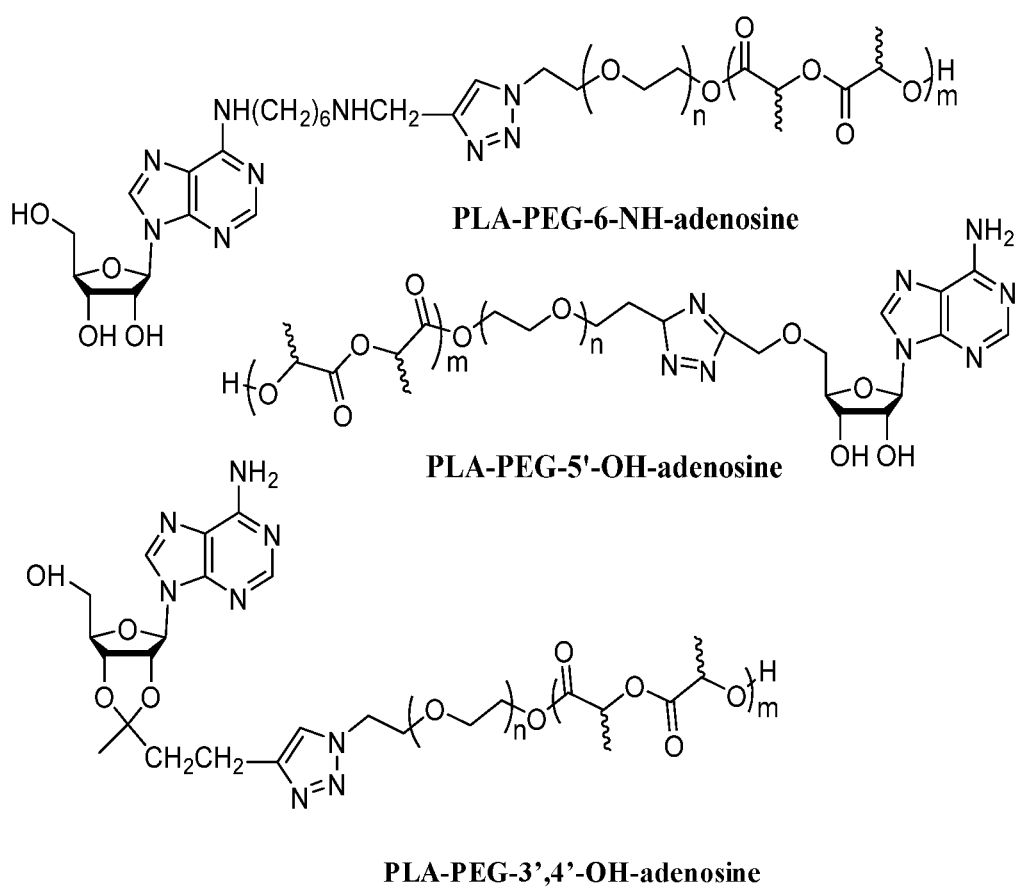
FIG. 2 shows the conjugation of alkynated adenosine through the 3' and 4' OH groups, through the 5' OH group, and through the amine group to PLA-b-PEG-$N_3$ copolymer.
Figures 3A, 3B, 3C, 3D:
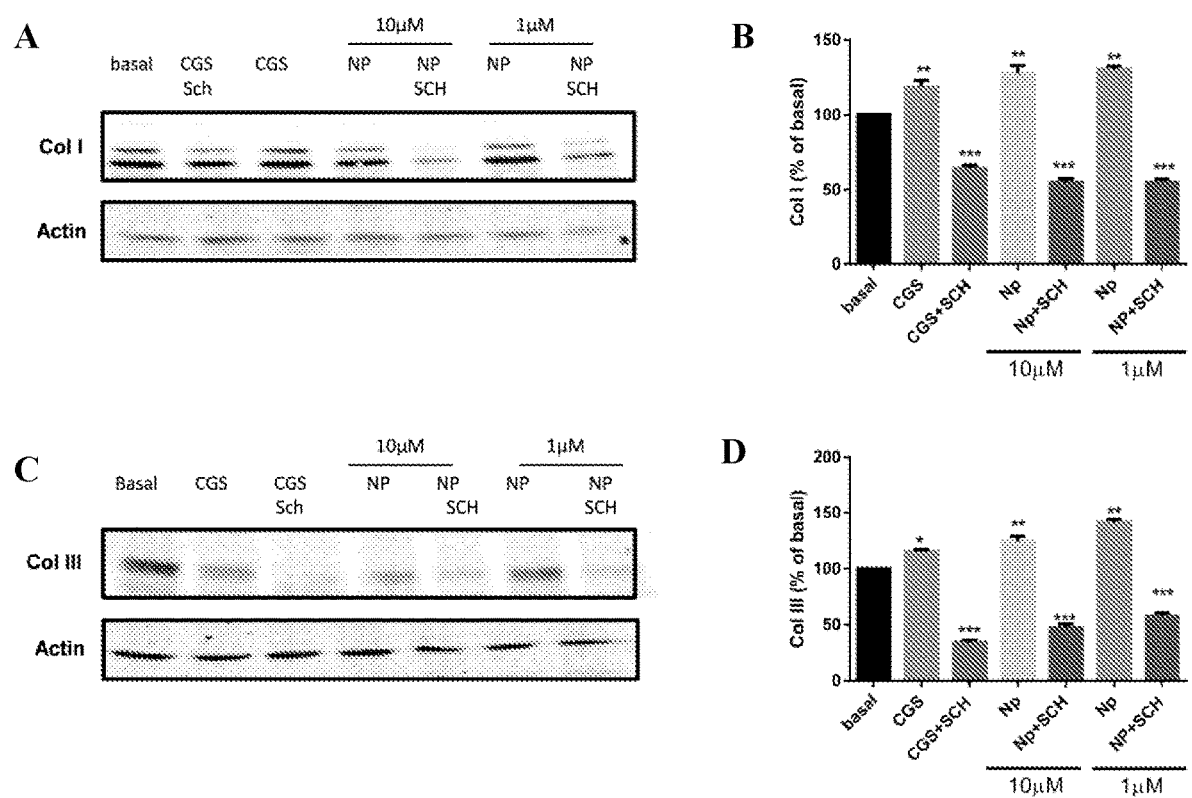
FIGS. 3A-3D show results demonstrating that culture of primary human dermal fibroblasts with nanoparticle-adenosine conjugates stimulated an increase in Collagen I and Collagen III production. 70% confluent NHDF (normal human dermofibrobast) were preincubated for 30 minutes in the presence of 10-6M SCH58261 (A2AR antagonist), and then in the presence of either $10^{-6}$ M CGS21680 (A2AR agonist) or nanoparticles containing Adenosine (NP) at doses 10 μM and 1 μM for 4 hours (n=4). Proteins were quantified and Collagen I (FIGS. 3A and 3B) and III (FIGS. 3C and 3D) expression was quantified by Western Blot. Both concentrations of nanoparticles induced Collagen I and III expression and this was reversed in the presence of the A2AR antagonist.

In yet another embodiment, T is functionalized on one or more sugar hydroxyl groups. In a further embodiment, T is functionalized on one or more sugar hydroxyl groups with a group having an acetylenic moiety. In a further embodiment, T is functionalized on a purine amino group. In a further embodiment, T is functionalized on a purine amino group with a group having an acetylenic moiety. Click chemistry techniques known in the art can then be used to attach T to a polymeric nanoparticle core, and prepare nanoparticles. Examples of adenosine attached through the 3' and 4' OH groups, the 5' OH group, and the purine $NH_2$ group to prepare a polymeric nanoparticle conjugate are shown in FIG. 2. In certain embodiments, T is functionalized on one or more sugar hydroxyl groups corresponding to the 3'-OH, 4'-OH, or —$CH_2$—OH attached to 5' position of the sugar (according to the nomenclature set forth herein; see FIG. 13). In certain embodiments, T is functionalized on sugar hydroxyl groups corresponding to the 3'-OH and 4'-OH groups of the sugar. In certain embodiments, T is functionalized on a sugar hydroxyl group corresponding to the —$CH_2$—OH attached to 5' position of the sugar. In certain embodiments, T is functionalized on a purine amino group corresponding to the $NH_2$ group attached to Carbon 6 in FIG. 13.

In yet another embodiment, at least one therapeutic agent T is an A2A adenosine receptor agonist. Examples of A2A receptor agonists include Molecules I and II and many of the agonists described above.

Where multiple different therapeutic agents T are used, combination therapy can be achieved, whereby treatment having greater efficacy and/or diminished side effects is obtained relative to the use of the therapeutically relevant dose of each agent alone.

In another embodiment, all therapeutic agents T are the same.

In a further embodiment, one of L and T comprises an azido group and the other of L and T comprises an alkyne group suitable for covalent attachment by a click chemistry reaction. For example, a "clickable" polymeric nanoparticle core can be reacted via $Cu^{1+}$ catalysis with an alkynated therapeutic agent T to provide a general platform for the attachment of any alkyne derivative of T. A description of click chemistry coupling is described, for example, in the Examples below.

In yet another embodiment, T is covalently linked to L via a 1,2,3-triazole linkage.

In a further embodiment, at least one occurrence of T is covalently linked to L through one or more sugar OH groups of T. Exemplary sugar OH groups that can be used to covalently link T to L can include —OH and/or —$CH_2$—OH groups attached to any one or more of the carbon atoms marked with * and **, as shown in the following exemplary generic sugar moiety:

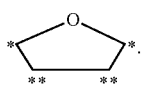

In certain embodiments sugar OH groups that can be used to covalently link T to L include —OH groups attached to the carbon atoms marked with **, as shown above. In certain embodiments, a sugar OH group that can be used to covalently link T to L includes a —$CH_2$—OH group attached to either carbon atom marked with *, as shown above.

In yet another embodiment, at least one occurrence of T is covalently linked to L through a purine $NH_2$ group.

Although particular examples of covalent linkage of T to L are described herein, any suitable covalent linkage chemistry may be used based on the selection of T and L. Moreover, the linker L can be attached to core polymeric matrix P and then therapeutic agent T can be covalently linked to L, or linker L can be covalently linked to therapeutic agent T, and then core polymeric matrix P can be attached to linker L.

In another embodiment, the diameter of the core polymeric matrix is from about 10 nm to about 250 nm, although other size ranges or distributions of size ranges are encompassed herein. In order to create nanoparticles of different sizes, the stoichiometry of the polymer for the polymer matrix and linker can be altered when forming a surface functionalized core polymeric matrix. By adjusting the ratio of polymer for the polymer matrix and linker, a large variety of polymeric nanoparticle conjugates can be prepared, providing tunable, multifunctional nanoparticles with different core sizes. Core size can be determined by any suitable technique including, for example, light scattering.

While it may be possible for the polymeric nanoparticle conjugates of the invention to be administered directly, it will often be preferable to present them as part of a pharmaceutical composition. Accordingly, another aspect of the present invention is a pharmaceutical composition containing a pharmaceutically acceptable carrier and the polymeric nanoparticle conjugate. The carrier must be "acceptable" in the sense of being compatible with the other ingredients of the formulation and not deleterious to the recipient thereof. A "pharmaceutically acceptable carrier" is intended to include one or more inert excipients, which include starches, polyols, granulating agents, microcrystalline cellulose, diluents, lubricants, binders, disintegrating agents, and the like.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the polymeric nanoparticle conjugates to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

Solid carriers suitable for use in the composition of the invention include one or more substances which may also act as flavoring agents, lubricants, solubilizers, suspending agents, fillers, glidants, compression aides, binders, tablet-disintegrating agents, or encapsulating materials. In powders, the carrier may be a finely divided solid which is in admixture with a finely divided compound of the present invention. In tablets, the polymeric nanoparticle conjugate may be mixed with a carrier having the necessary compression properties in suitable proportions and compacted in the shape and size desired. Said powders and tablets may contain up to 99% by weight of the polymeric nanoparticle conjugate. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Any pharmaceutically acceptable liquid carrier suitable for preparing solutions, suspensions, emulsions, syrups and elixirs may be employed in the composition of the invention. Polymeric nanoparticle conjugates may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and *arachis* oil). For parenteral administration the carrier may also be an oily ester such as ethyl oleate or isopropyl myristate.

Another aspect of the present invention relates to a method of treating and/or preventing arthritis in a patient in need thereof. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an A2A adenosine receptor agonist, an A2B adenosine receptor agonist, and an A3 adenosine receptor agonist.

In one embodiment, the arthritis is osteoarthritis, a non-inflammatory or non-immune condition. Osteoarthritis does not involve Type I hypersensitivity or Type IV hypersensitivity reactions.

In a particular embodiment, the polymeric nanoparticle conjugate may be administered intraarticularly.

In a further particular embodiment, the present invention relates to the treatment and/or prevention of osteoarthritis through stimulation of adenosine receptors on chondrocytes. Chondrocytes are the cells that synthesize and maintain cartilage and which are primarily affected in osteoarthritis. This stimulation suppresses the effects of inflammation on these cells.

Yet another aspect of the present invention relates to a method of treating a wound in a patient in need thereof. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an A2A adenosine receptor agonist, an A2B adenosine receptor agonist, and an A3 adenosine receptor agonist.

In one embodiment, the wound is a burn, an ischemic ulcer, a decubitus ulcer, an ulcer resulting from an infectious process, an ulcer resulting from an inflammatory processes, a surgical wound, or a diabetic foot ulcer.

A further aspect of the present invention relates to a method of treating and/or preventing a dermatological condition in a patient in need thereof. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an A2A adenosine receptor agonist, an A2B adenosine receptor agonist, and an A3 adenosine receptor agonist.

In one embodiment, the dermatological condition is wrinkles, inflammatory skin conditions, psoriasis, eczema, or dermatosis. The polymeric nanoparticle conjugate may, in one particular embodiment, be administered subcutaneously to further promote collagen production and reduce wrinkling, thereby giving a more youthful appearance to the skin.

Another aspect of the present invention relates to method of treating a joint to promote surgical healing. This method involves selecting a subject in need of treatment, and administering to the selected subject a therapeutically acceptable amount of a polymeric nanoparticle conjugate comprising a polymeric nanoparticle core conjugated to one or more therapeutic agents, wherein at least one therapeutic agent is selected from the group consisting of adenosine, an adenosine derivative, an adenosine analogue, an A2A adenosine receptor agonist, an A2B adenosine receptor agonist, and an A3 adenosine receptor agonist.

In one particular embodiment, polymeric nanoparticle conjugates can be administered topically during surgery (e.g., tendon repair, Rotator cuff surgery) to enhance healing of the wounds, joints, or of the repaired ligaments, tendons, etc.

As used in the methods described herein, a therapeutically acceptable amount is an amount sufficient to decrease or prevent the symptoms associated with the conditions disclosed herein. Such effective amounts may be determined using routine optimization techniques and are dependent on the particular condition to be treated, the condition of the subject, the route of administration, the formulation, and the judgment of the practitioner and other factors evident to those skilled in the art.

The amount of therapeutic agent to produce a single dosage form will vary depending upon the host treated and the particular mode of administration. For example, a formulation intended for the intraarticular administration of humans may vary from about 5 to about 95% of the total composition.

The conjugates according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, week, month, etc, in accordance with the physiological requirements of each particular patient and depending upon the mode of administration.

Exemplary routes of administration include, without limitation, orally, parenterally, periadventitially, subcutaneously, intravenously, intramuscularly, intraarticularly, intraperitoneally, by inhalation, by intranasal instillation, by implantation, by intracavitary or intravesical instillation, intraocularly, intraarterially, intralesionally, topically, transdermally, or by application to mucous membranes.

Exemplary polymeric nanoparticle cores in accordance with the methods of the present invention are biodegradable and comprise a polymeric matrix having surface hydrophilic polymer moieties as described above with regard to core polymer matrix P and surface linker group L. At least one therapeutic agent is covalently linked to the surface hydrophilic polymer moieties, as described above with regard to therapeutic agent T.

In a particular embodiment, adenosine derivatives can be prepared according to Scheme 1 shown below.

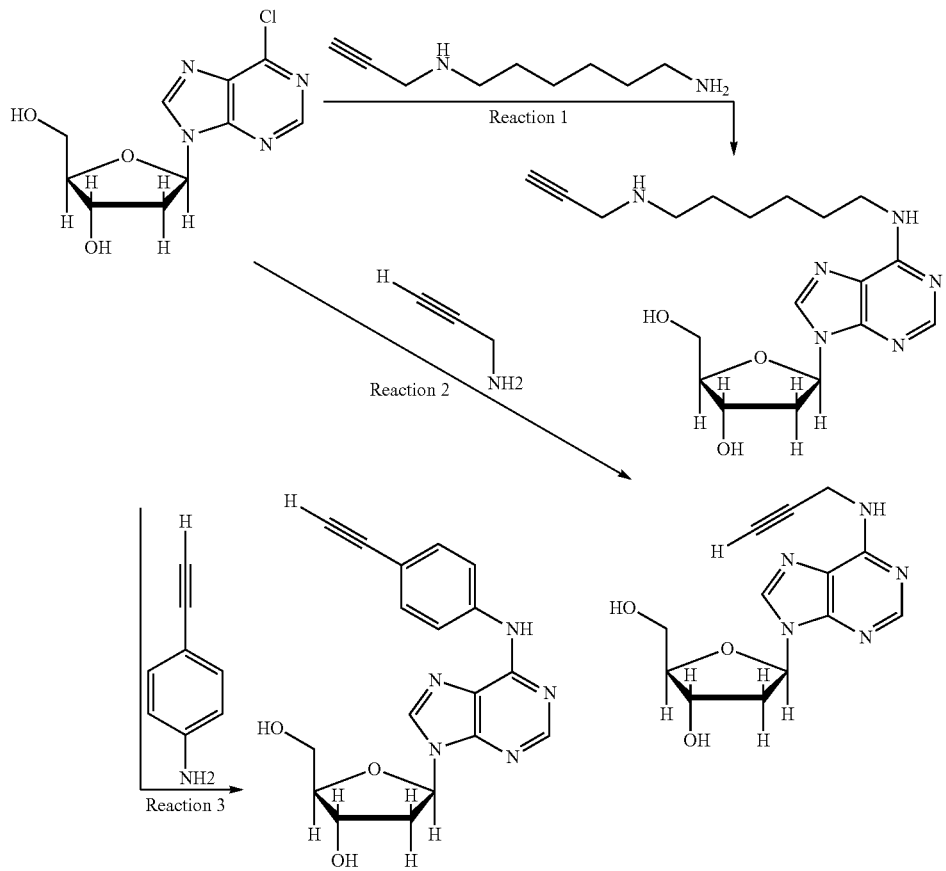

Scheme 1.

Adenosine can be functionalized on the purine amino group with group carrying acetylenic moiety, which provides facile click chemistry with an already prepared azide-functionalized PLA-PEG diblock copolymer.

All described routes in Scheme 1 start from 6-chloropurine 9-β-D-ribofuranoside (CAS Registry Number 5399-87-1), which is commercially available. Three derivatives can be prepared by the reaction of 6-chloropurine 9-β-D-ribofuranoside with an amine.

According to reaction 1, $N^1$-(prop-2-yn-1-yl)hexane-1,6-diamine (CAS Registry Number 90728-65-7, which can be prepared according to the method described in GB Patent No. 903,200 to Sterling Drug Inc., each of which is hereby incorporated by reference in its entirety) is reacted with 6-chloropurine 9-β-D-ribofuranoside according to the method described in Koh et al., "SAR Analysis of Adenosine Diphosphate (Hydroxymethyl) pyrrolidinediol Inhibition of Poly(ADP-ribose) Glycohydrolase," *J. Med. Chem.*, 46(20): 4322-4332 (2003) and Bridges et al., "N6-(2,2-diphenylethyl)adenosine, a novel adenosine receptor agonist with antipsychotic-like activity," *J. Med. Chem.*, 30: 1709-11 (1987), which are hereby incorporated by reference in their entirety.

According to reaction 2,2-propyn-1-amine (CAS Registry Number 2450-71-7), which is commercially available is reacted with 6-chloropurine 9-β-D-ribofuranoside, as described in Koh et al., "SAR Analysis of Adenosine Diphosphate (Hydroxymethyl) pyrrolidinediol Inhibition of Poly(ADP-ribose) Glycohydrolase," *J. Med. Chem.*, 46(20): 4322-4332 (2003) and Bridges et al., "N6-(2,2-diphenylethyl)adenosine, a novel adenosine receptor agonist with antipsychotic-like activity," *J. Med. Chem.*, 30: 1709-11 (1987), which are hereby incorporated by reference in their entirety.

According to reaction 3,4-aminophenylacetylene (CAS Registry Number 14235-81-5), which is commercially available is reacted with 6-chloropurine 9-β-D-ribofuranoside according to the method described in Bridges et al., "N6-(2,2-diphenylethyl)adenosine, a novel adenosine receptor agonist with antipsychotic-like activity," *J. Med. Chem.*, 30: 1709-11 (1987) and Kwatra et al., "N6-Phenyladenosines: pronounced effect of phenyl substituents on affinity for A2 adenosine receptor," *J. Med. Chem.*, 30: 954-6 (1987), which are hereby incorporated by reference in their entirety.

The three new adenosine derivatives can then react with a polymeric nanoparticle core (such as PLA-b-PEG-$N_3$ copolymers), and the resulting products can be used as adenosine-functionalized biodegradable nanoparticles.

In one embodiment, adenosine-functionalized biodegradable nanoparticles can be prepared according to Scheme 2 shown below.

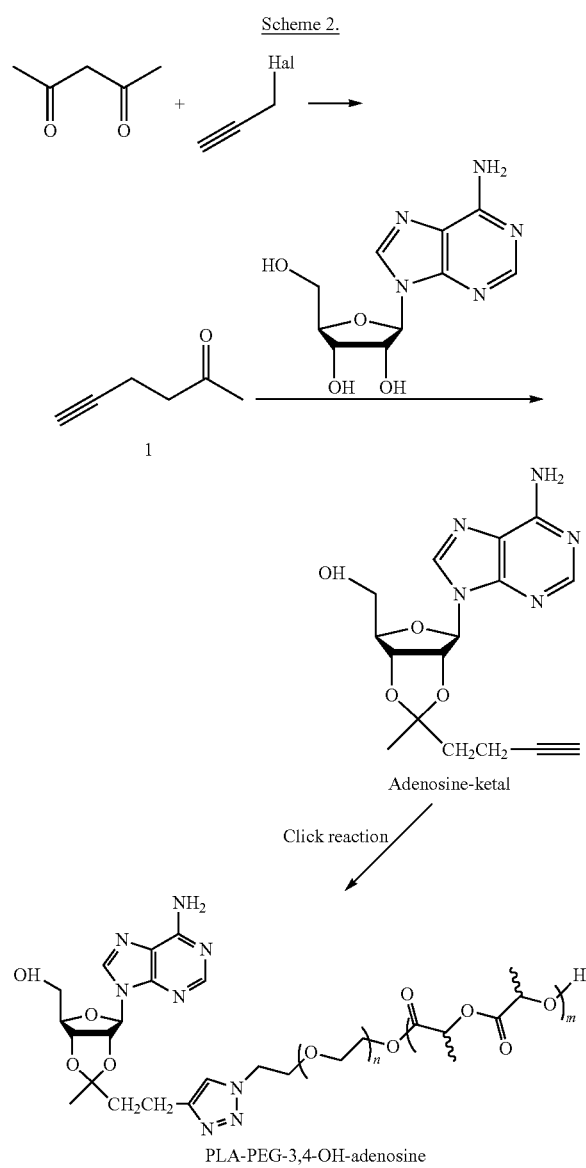

According to Scheme 2, 2,4-pentanedione is first reacted with propargyl halide in the presence of base to form 5-hexyn-2-one. The reaction can be carried out in a variety of solvents, for example in ethanol (EtOH), methanol (MeOH), acetonitrile (CH$_3$CN), methylene chloride (CH$_2$Cl$_2$), tetrahydrofuran (THF), dimethylformamide (DMF), or other such solvents or in the mixture of such solvents. In one embodiment, the propargyl halide is propargyl chloride. Exemplary base is anhydrous potassium carbonate. Formed 5-hexyn-2-one is then reacted with adenosine to form adenosine-ketal. The reaction can be carried out in a variety of solvents, for example in ethanol (EtOH), methanol (MeOH), acetonitrile (CH$_3$CN), methylene chloride (CH$_2$Cl$_2$), tetrahydrofuran (THF), dimethylformamide (DMF), dioxane, or other such solvents or in the mixture of such solvents. In some embodiments this reaction is carried out in the presence of triethyl orthoformate. PLA-PEG-3,4-OH-adenosine (which may also be referred to as PLA-PEG-3',4'-OH-adenosine) is then prepared by click reaction between adenosine-ketal and corresponding azide.

Click reaction between adenosine-ketal and corresponding azide can be performed in a variety of solvents, for example in ethanol (EtOH), methanol (MeOH), acetonitrile (CH$_3$CN), dimethyl formamide (DMF), tetrahydrofuran (THF), toluene, dimethylsulfoxide (DMSO), water, or other such solvents or in the mixture of such solvents (Meldal et al., "Cu-Catalyzed Azide-Alkyne Cycloaddition," Chem. Rev. 108(8):2952-3015 (2008), which is hereby incorporated by reference in its entirety). The reaction can be conducted at a temperature between the room temperature and the reflux temperature of the reaction mixture. The reaction can be carried out in the presence of the copper source. Suitable copper source include, but are not limited to, CuI, CuCl, CuBr, CuSO$_4$, CuCl$_2$, and ect. Suitable base that can be used in this reaction include, but are not limited to, N,N-Diisopropylethylamine (DIPEA), Na$_2$CO$_3$, 1,8-Diazabicycloundec-7-ene (DBU), triethylamine (TEA), and ect. Suitable ligands that can be used in this reaction include, but are not limited to, N,N,N',N',N''-pentamethyl-diethylenetriamine (PMDETA), tris[(1-benzyl-1H-1,2,3-triazol-4-yl)methyl]amine (TBTA), 2,2'-bipyridine (bipy), and ect. The presence of a reducing agent for the catalyst, such as sodium ascorbate may be advantageous.

In another embodiment, adenosine-functionalized biodegradable nanoparticles can be prepared according to Scheme 3 shown below.

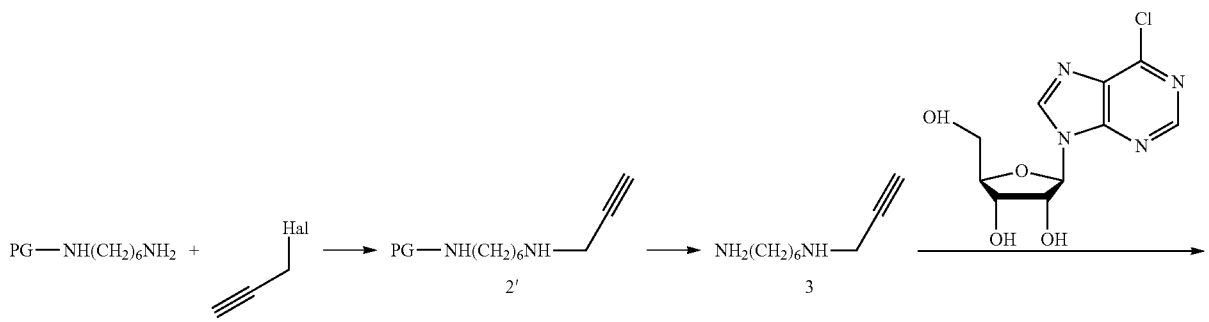

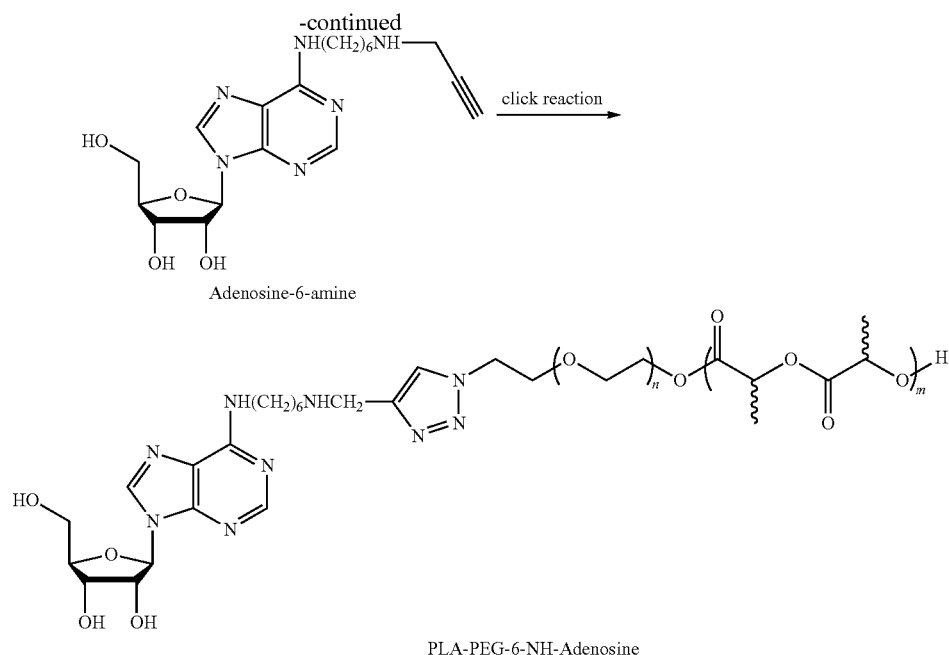

Adenosine-6-amine

PLA-PEG-6-NH-Adenosine

According to Scheme 3, propargyl halide is first reacted with protected amine in the presence of base to form compound 2'. The reaction can be carried out in a variety of solvents, for example in ethanol (EtOH), methanol (MeOH), acetonitrile (CH$_3$CN), methylene chloride (CH$_2$Cl$_2$), tetrahydrofuran (THF), dimethylformamide (DMF), or other such solvents or in the mixture of such solvents. The reaction can be carried out at room temperature or at elevated temperatures. In one embodiment, the propargyl halide is propargyl chloride. Useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbony, 2-(trichlorosilyl) ethoxycarbonyl, 9-fluorenylmethoxycarbonyl (Fmoc), phthaloyl, acetyl (Ac), formyl, trifluoroacetyl, and the like. In one embodiment, the protected amine is Boc-protected amine. Exemplary base is anhydrous potassium carbonate. Following removal of the protecting group, amine 3 is reacted with adenosine to form adenosine-6-amine in the presence of the base. The reaction can be carried out in a variety of solvents, for example in ethanol (EtOH), methanol (MeOH), acetonitrile (CH$_3$CN), methylene chloride (CH$_2$Cl$_2$), tetrahydrofuran (THF), dimethylformamide (DMF), or other such solvents or in the mixture of such solvents. PLA-PEG-6-NH-adenosine is then prepared by a click reaction between adenosine-6-amine and corresponding azide.

Click reaction between adenosine-6-amine and corresponding azide can be performed in a variety of solvents, for example in ethanol (EtOH), methanol (MeOH), acetonitrile (CH$_3$CN), dimethyl formamide (DMF), tetrahydrofuran (THF), toluene, dimethylsulfoxide (DMSO), water, or other such solvents or in the mixture of such solvents (Meldal et al., "Cu-Catalyzed Azide-Alkyne Cycloaddition," *Chem. Rev.* 108(8):2952-3015 (2008), which is hereby incorporated by reference in its entirety). The reaction can be conducted at a temperature between the room temperature and the reflux temperature of the reaction mixture. The reaction can be carried out in the presence of the copper source. Suitable copper source include, but are not limited to, CuI, CuCl, CuBr, CuSO$_4$, CuCl$_2$, and ect. Suitable base that can be used in this reaction include, but are not limited to, N,N-Diisopropylethylamine (DIPEA), Na$_2$CO$_3$, 1,8-Diazabicycloundec-7-ene (DBU), triethylamine (TEA), and ect. Suitable ligands that can be used in this reaction include, but are not limited to, N,N,N',N',N"-pentamethyl-diethylenetriamine (PMDETA), tris[(1-benzyl-1H-1,2,3-triazol-4-yl)methyl] amine (TBTA), 2,2'-bipyridine (bipy), and ect. The presence of a reducing agent for the catalyst, such as sodium ascorbate may be advantageous.

In yet another embodiment, adenosine-functionalized biodegradable nanoparticles can be prepared according to Scheme 4 shown below.

Scheme 4.

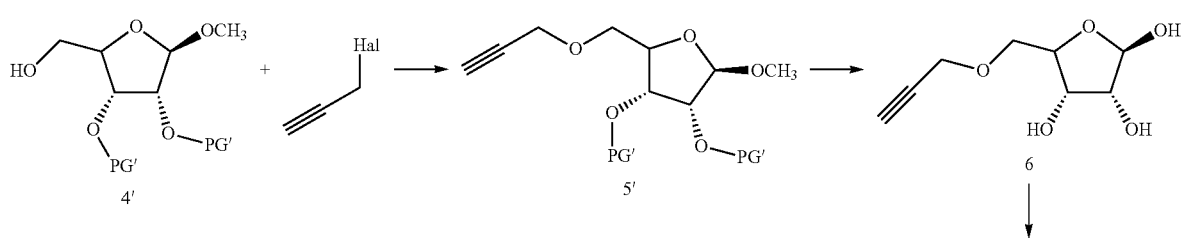

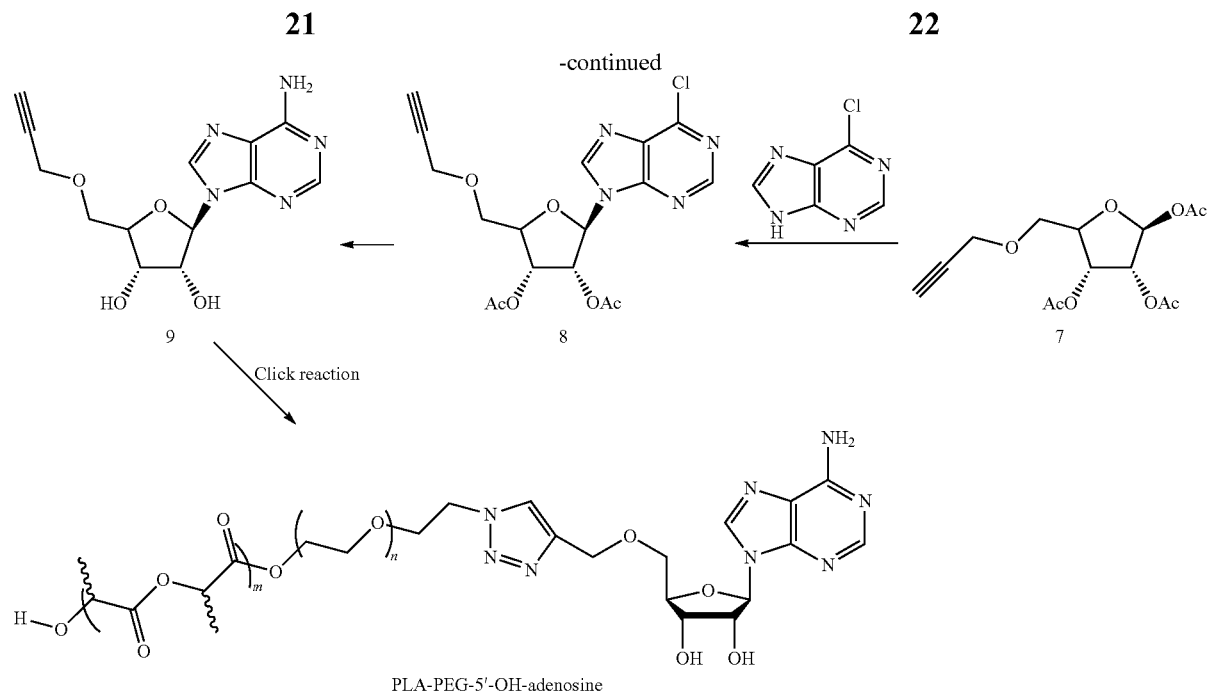

PLA-PEG-5'-OH-adenosine

According to Scheme 4, compound 4' is first reacted with propargyl halide in the presence of base to form compound 5'. The reaction can be carried out in a variety of solvents, for example in ethanol (EtOH), methanol (MeOH), acetonitrile ($CH_3CN$), methylene chloride ($CH_2Cl_2$), tetrahydrofuran (THF), dimethylformamide (DMF), or other such solvents or in the mixture of such solvents. In one embodiment, the propargyl halide is propargyl chloride. Exemplary base is sodium hydride. Following removal of the protecting group, compound 6 is acylated and then reacted with silylated 6-chloropurine to form compound 8. The reaction can be carried out in a variety of solvents, for example in 1,2-dichloroethane, acetonitrile ($CH_3CN$), methylene chloride ($CH_2Cl_2$), tetrahydrofuran (THF), dimethylformarnide (DMF), or other such solvents or in the mixture of such solvents. PLA-PEG-5'-OH-adenosine is then prepared by a click reaction between compound 9, formed by deprotecting compound 8, and corresponding azide.

Click reaction between compound 9 and corresponding azide can be can be performed in a variety of solvents, for example in ethanol (EtOH), methanol (MeOH), acetonitrile ($CH_3CN$), dimethyl formamide (DMF), tetrahydrofuran (THF), toluene, dimethylsulfoxide (DMSO), water, or other such solvents or in the mixture of such solvents (Meldal et al., "Cu-Catalyzed Azide-Alkyne Cycloaddition," Chem. Rev. 108(8):2952-3015 (2008), which is hereby incorporated by reference in its entirety). The reaction can be conducted at a temperature between the room temperature and the reflux temperature of the reaction mixture. The reaction can be carried out in the presence of the copper source. Suitable copper source include, but are not limited to, CuI, CuCl, CuBr, $CuSO_4$, $CuCl_2$, and ect. Suitable base that can be used in this reaction include, but are not limited to, N,N-Diisopropylethylamine (DIPEA), $Na_2CO_3$, 1,8-Diazabicycloundec-7-ene (DBU), triethylamine (TEA), and ect. Suitable ligands that can be used in this reaction include, but are not limited to, N,N,N',N',N''-pentamethyl-diethylenetriamine (PMDETA), tris[(1-benzyl-1H-1,2,3-triazol-4-yl)methyl]amine (TBTA), 2,2'-bipyridine (bipy), and ect. The presence of a reducing agent for the catalyst, such as sodium ascorbate may be advantageous.

EXAMPLES

Example 1—Synthesis of 1-Hexyne-5-one

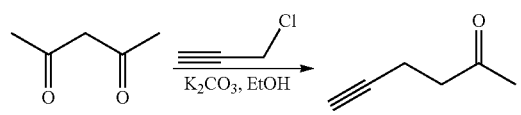

A mixture of propargyl chloride (53.2 g, 0.5 mol), acetylacetone (55.1 g, 0.55 mol), $K_2CO_3$ (77.4 g, 0.56 mol), and 300 mL of EtOH was refluxed overnight. Most of the EtOH was removed by atmospheric distillation. The mixture was taken up in MTBE and washed with water. The extracts were dried with $MgSO_4$ and concentrated by simple distillation. House vacuum distillation gave the desired product (20.0 g, 38% yield). $^{13}C$ NMR ($CDCl_3$): 206.3, 82.9, 68.7, 41.97, 29.7, 12.8 ppm. See Görl, "The Combination of Mononuclear Metallocene and Phenoxyimine Complexes to Give Trinuclear Catalysts for the Polymerization of Ethylene," J. Organometallic Chemistry 692: 5727-5753 (2007), which is hereby incorporated by reference in its entirety.

Example 2—Synthesis of 1-Hexyne-5-one with Adenosine

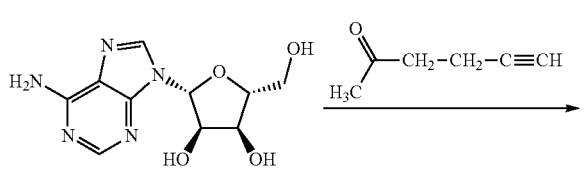

-continued

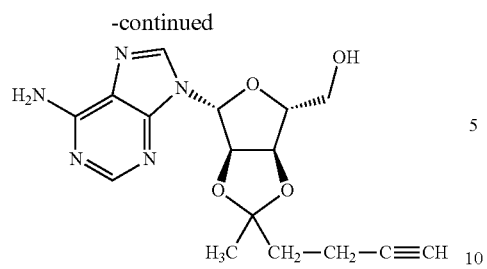

To a suspension of adenosine (2.81 g, 10.5 mmol) in dry DMF-dimethyl formamide (35 ml), 1-hexyne-5-one (1.01 g, 22.6 mmol) and triethyl orthoformate (1.56 g) were added, and insoluble material was dissolved by adding a solution of 4 M hydrogen chloride in dry p-dioxane (8 ml). The mixture was kept 24 hours at room temperature and then poured into dry diethyl ether (400 ml). The upper layer was decanted, and the oily residue was washed with ether and then dissolved in chloroform by addition of 2% aqueous sodium hydrogencarbonate. The organic layer was washed with water, dried, and concentrated, and the residue was chromatographed on silica gel using first chloroform as eluent, and then 10:1 $CHCl_3$:$CH_3OH$. The yield was 0.51 g·mp 227° C. See Ott et al., "R- and S-alkylidene Acetals of Adenosine: Stereochemical Probes for the Active Site of Adenosine Deaminase," *Bioorg. Chem.* 10:82-89 (1981), which is hereby incorporated by reference in its entirety.

Example 3—Synthesis of PEG-Tos

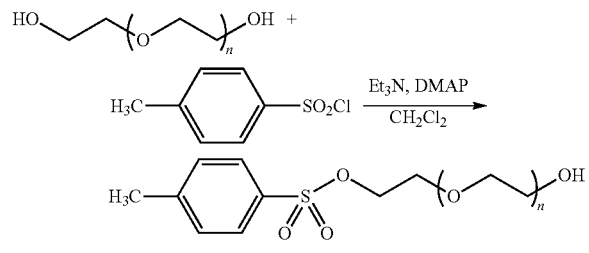

In a typical synthesis, 3.0 g of PEG (MW 2050) were dissolved in 100 ml toluene and azeotroped for 2 hours until no more water could be recovered. The solution was cooled to room temperature and the toluene was removed under vacuum. The dry PEG was dissolved in 20 ml dry $CH_2Cl_2$, 0.71 g of triethyl amine was added and 0.86 g 4-dimethylaminopyridine. The reaction vessel was put in an ice bath and the solution was stirred for 15 minutes. To the cold (4-5° C.) solution was added dropwise a solution of 1.34 g p-toluene sulfonyl chloride in 30 ml dry $CH_2Cl_2$. The reaction mixture was stirred overnight, and then the $CH_2Cl_2$ was removed and the residue was dissolved in a minimum amount of $CHCl_3$. 25 g silica were used in a column using $CHCl_3$ to remove the ditosylate. The polarity of the eluent was increased by using 5% $CH_3OH$ in methanol, were by the monotosylate was separated. The yield was 2.75 g. See Mahou et al., "Versatile Route to Synthesize Heterobifunctional Poly(ethylene glycol) of Variable Functionality for Subsequent Pegylation," *C. Polymers* 4:561-589 (2012), which is hereby incorporated by reference in its entirety.

Example 4—Synthesis of PEG-$N_3$

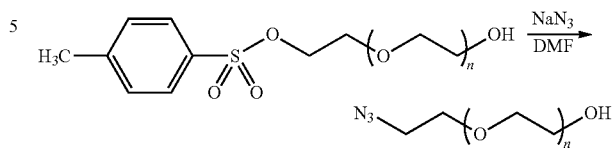

2 g of PEG-Tos were dissolved in 15 ml of dry DMF and 0.3 g of $NaN_3$ was added. The reaction mixture was allowed to stir at 70° C. for 24 hours. The DMF was removed under vacuum, and the product was dissolved in 40 ml of $CHCl_3$ and washed with saturated NaCl solution, 3 times, each with 60 mL of the salt solution. The chloroform was removed by rotary evaporator and the product was dissolved in 7 ml dry $CH_2Cl_2$ and added dropwise to 100 ml dry ether under magnetic stirring. The solution was left overnight in the freezer. The solid was separated by filtration and allowed to dry. The yield was 72%. See Mahou et al., "Versatile Route to Synthesize Heterobifunctional Poly(ethylene glycol) of Variable Functionality for Subsequent Pegylation," *C. Polymers* 4:561-589 (2012), which is hereby incorporated by reference in its entirety.

Example 5—Synthesis of PLA-b-PEG-$N_3$

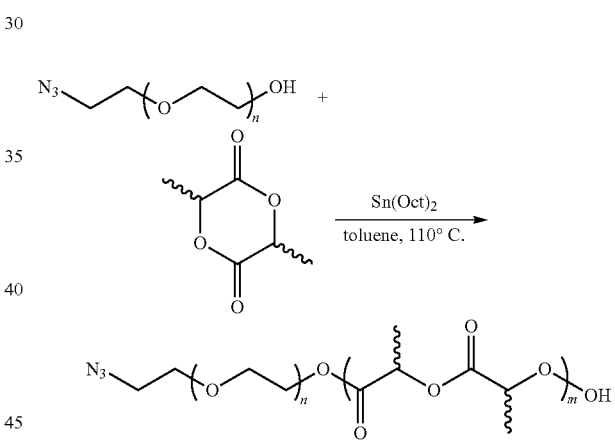

To a mixture of HO-PEG-$N_3$ (293 mg, 0.12 mmol) and D,L-lactide (7.2 g, mmol) was added, in dry conditions, a solution of $Sn(Oct)_2$ (110 mg, 46.1 µmol) in anhydrous toluene (15 mL). The reaction mixture was degassed by bubbling nitrogen for 20 min and then stirred in a pre-heated oil bath at 120° C. for 2 hours under inert atmosphere. The reaction mixture was allowed to stir at room temperature overnight. Toluene was removed under reduced pressure and the obtained product was dissolved into a minimum volume of $CH_2Cl_2$, and subsequently precipitated in $Et_2O$. The precipitate was then dissolved into a minimum amount of THF and further precipitated in water and subsequently freeze-dried overnight to yield a white powder. ($M_{n,NMR}$=30,080 g·mol$^{-1}$, $M_{n,SEC}$=20100 g·mol$^{-1}$, Đ=1.11). $^1$H NMR (400 MHz, CDCl$_3$, δ in ppm): 5.41-4.83 (m, 377H), 4.38-4.15 (m, 3H), 3.84-3.40 (m, 222H), 3.36 (t, J=4.8 Hz, 2H), 1.82-1.21 (m, 1132H). See Zhang et al., "Synthesis and Characterization of the Paclitaxel/MPEG-PLA Block Copolymer Conjugate," *Biomaterials* 26:2121-2128 (2005), which is hereby incorporated by reference in its entirety.

Example 6—Conjugation of Alkynated Adenosine to PLA-b-PEG-N₃ Copolymer

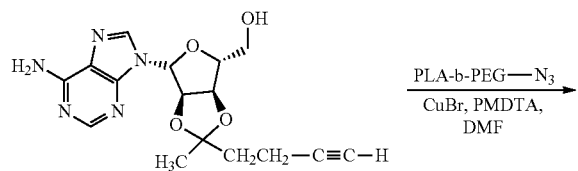

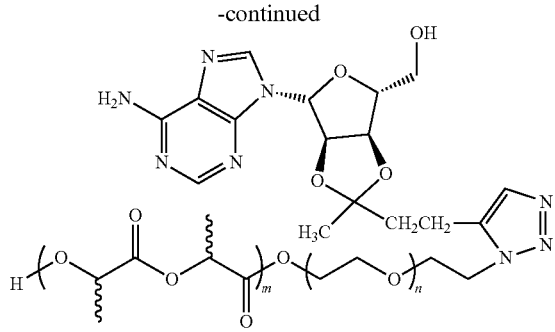

In a three-neck flask were placed 69 mg of adenosine ketone adduct and 330 mg of PLA-b-PEG-N₃. The flask was flushed with nitrogen for 20 min, and a solution of 11 mg CuBr and 31 mg N,N,N',N',N''-pentamethyldiethylenetriamine (PMDTA) in 2.8 ml dry DMF was added, and the reaction mixture was stirred for 15 hours at 40° C. The DMF and PMDTA were removed under reduced pressure, and the resulting solid was dissolved in a minimum volume of DMC, and was added dropwise under stirring to a 10 fold volume of dry ethyl ether. The resulting solution was left overnight in the freezer. The solid was separated by filtration, giving 275 mg. The product was dissolved in a minimum volume of dry THF and the solution was stored in the freezer. See Mackiewicz et al., "Precise Engineering of Multifunctional PEGylated Polyester Nanoparticles for Cancer Cell Targeting and Imaging," *Chem. Mater.* 26: 1834-1847 (2014), which is hereby incorporated by reference in its entirety.

Example 7—Preparation of PLA-b-PEG-Adenosine Nanoparticles 30 mg PLA-b-PEG-Adenosine were dissolved in 1.2 ml ethyl acetate. The solution was added to a 3.3. ml 1% Pluronic F68 solution, and vortex was used to ensure complete mixing. The resulting solution was ultrasonicated for 3 min at 45% amplitude, using a sharp tip. The ethyl acetate was removed under vacuum, and the water suspension was centrifuged at 14,000 RPM for 1 hour. The water was decanted and the solid was suspended in 3 ml of PBS pH 7.4 and was passed through a 0.45μ filter. See Mackiewicz et al., "Precise Engineering of Multifunctional PEGylated Polyester Nanoparticles for Cancer Cell Targeting and Imaging," *Chem. Mater.* 26: 1834-1847 (2014), which is hereby incorporated by reference in its entirety.

Example 8—Synthesis of PCL-b-PEG-N₃

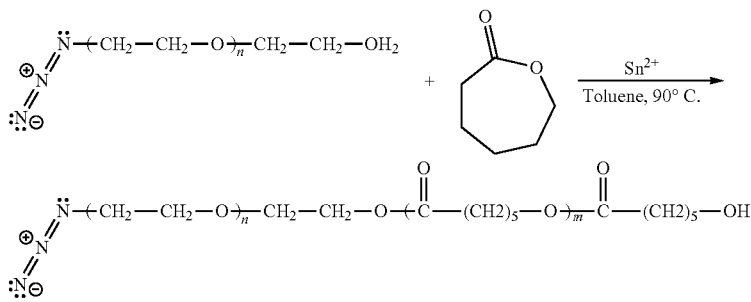

PCL-b-PEG-N₃ copolymer was prepared as described in Example 5 for PLA-b-PEG-N₃.

Example 9—Synthesis of α-Methoxyl-ω-hydroxyl PEG

Glassware was silanized by rinsing with a 5% methyltrichlorosilane solution in toluene, then with acetone, and finally dried overnight at 130° C. (Bensaid et al., "Y-shaped mPEG-PLA Cabazitaxel Conjugates: Well-Controlled Synthesis by Organocatalytic Approach and Self-Assembly Into Interface Drug-Loaded Core-Corona Nanoparticles," *Biomacromolecules* 14:1189-1198 (2013), which is hereby incorporated by reference in its entirety). To a mixture of MeO-PEG (293 mg, 0.12 mmol) and D,L-lactide (7.01 g, 48.62 mmol) a solution of Sn(Oct)₂ (2 drops) in anhydrous toluene (11.2 ml) was added, under dry conditions. The reaction mixture was degassed by vacuum and filled by nitrogen and then stirred in a preheated oil bath at 110° C. for 24 hours. Toluene was removed under reduced pressure, and the obtained product was dissolved into a minimum volume of DCM and subsequently precipitated in ethyl ether. The precipitate was then dissolved into a minimum amount of THF, further precipitated in water, filtered, and subsequently dried over vacuum overnight. (MeO-PEG550, $M_{n,NMR}$=18725 g/mol). ¹H NMR (500 MHz, CDCl₃): δ=5.21-5.15 (m, 300H, CH PLA), 3.73-3.80 (m, 4H), 3.63 (m, 58H, CH₂ PEG), 3.38 (s, 3H), 1.58 (m, 974H, CH₃ PLA)ppm. See Bensaid et al., "Y-Shaped mPEG-PLA Cabazitaxel Conjugates: Well-Controlled Synthesis by Organocatalytic Approach and Self-Assembly into Interface Drug-Loaded Core-Corona Nanoparticles," *Biomacromolecules*, 14: 1189-1198 (2013), which is hereby incorporated by reference in its entirety.

Example 10—Synthesis of α-Tosyl-ω-hydroxyl PEG

PEG, previously dried by azeotropic distillation in toluene using a Bean-Stark trap, was dissolved in 250 ml of dry toluene and Ag$_2$O (1.5 equiv, 4.8 g, 20.7 mmol) and KI (0.2 equiv, 458 mg, 2.76 mmol) were added (Mahou et al., "Versatile Route to Synthesize Heterobifunctional Poly(ethylene glycol) of Variable Functionality for Subsequent Pegylation," *Polymers*, 4:561-589 (2012), which is hereby incorporated by reference in its entirety). To this rapidly stirred solution p-toluene sulfonyl chloride (1.05 equiv, 2.76 g, 14.5 mmol) was added in one portion. The reaction mixture was constantly stirred at room temperature for 12 hours and then filtered over a filter cell cake. Solvent removal by rotary evaporation was performed. The crude product was dissolved in 20 ml dichloromethane and then precipitated by dropwise addition into diethyl ether, the polymer was collected by filtration (98%).

Example 11—Synthesis of α-Azide-ω-hydroxyl PEG

α-Tosyl-ω-hydroxyl PEG (10 g, 6.23 mmol) and NaN$_3$ (2 g, 31 mmol) were dissolved in 150 ml of dry DMF and the mixture was stirred at 90° C. under nitrogen for overnight (Mahou et al., "Versatile Route to Synthesize Heterobifunctional Poly(ethylene glycol) of Variable Functionality for Subsequent Pegylation," *Polymers*, 4:561-589 (2012), which is hereby incorporated by reference in its entirety). Then the DMF was removed under reduced vacuum. The crude product was dissolved in 100 ml DCM and washed twice with brine and twice with water. The organic layer was dried over sodium sulfate, reduced to small volume by rotary evaporation, and finally precipitated by dropping into diethyl ether. The polymer was collected by filtration.

Example 12—Synthesis of PLA-β-PEG-N$_3$

A typical synthesis is as follows. Glassware was silanized by rinsing with a 5% methyltrichlorosilane solution in toluene, then with acetone, and finally dried overnight at 130° C. To a mixture of HO-PEG400-N$_3$ or (HO-PEG2000-N$_3$) (0.12 mmol) and D,L-lactide (7.01 g, 48.62 mmol) was added, under dry condition, a solution of Sn(Oct)$_2$ (2 drops) in anhydrous toluene (11.2 ml). The reaction mixture was degassed by vacuum, filled by nitrogen, and then stirred in a preheated oil bath at 110° C. for 24 hours. Toluene was removed under reduced pressure, and the obtained product was dissolved into a minimum volume of DCM and subsequently precipitated in ethyl ether. The precipitate was then dissolved into a minimum amount of THF, further precipitated in water, and subsequently was dried over vacuum overnight. (PLA-PEG400-N$_3$, M$_{n,NMR}$=18975 g/mol. PLA-PEG2000-N$_3$, M$_{n,NMR}$=21890 g/mol) PLA-PEG2000-N$_3$, $^1$H NMR (500 MHz, CDCl$_3$): δ=5.21-5.15 (m, 30H, CH PLA), 3.76 (m, 2H, CH$_2$ PEG), 3.68 (m, 2H, PEG), 3.66 (m, 14H, PEG), 1.58 (m, 974H, CH$_3$ PLA).

Example 13—Synthesis of 5-Hexyn-2-one (Compound 1)

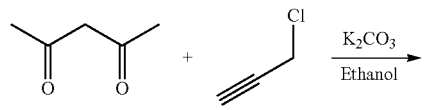

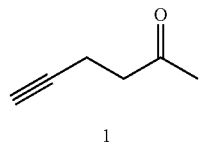

2,4-Pentanedione (100 g, 103 ml, 1 mol), anhydrous potassium carbonate (152 g, 1.1 mol), and propargyl chloride (71 g, 69 ml, 0.95 mol) were dissolved in 500 ml of ethanol. The reaction mixture was stirred under reflux for 24 hours (Görl et al., "The Combination of Mononuclear Metallocene and Phenoxyimine Complexes to Give Trinuclear Catalysts for the Polymerization of Ethylene," *J. Organimetallic Chemistry*, 692:5727-5753 (2007), which is hereby incorporated by reference in its entirety). After cooling to room temperature, 300 ml of water were added. The mixture was then extracted with diethyl ether, and the organic phase was washed with brine and dried over sodium sulfate. Removal of the solvent and subsequent vacuum distillation yielded 5-hexyn-2-one as colorless liquid in 48% yield.

Example 14—Synthesis of Adenosine-ketal

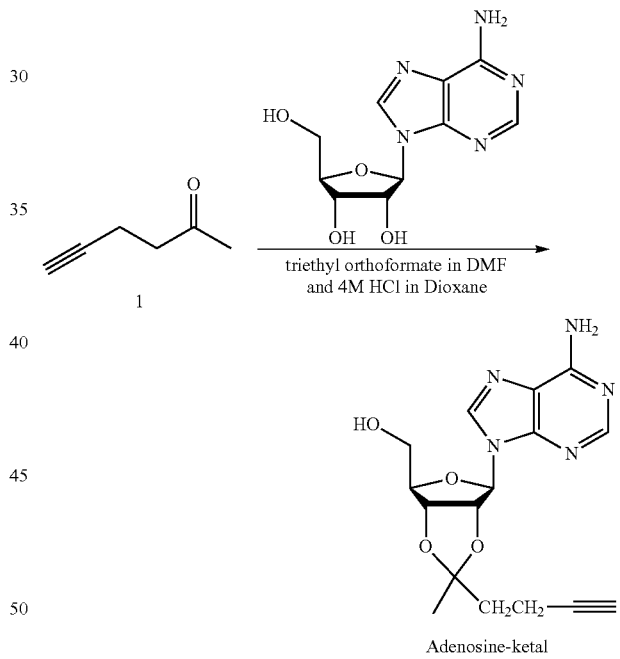

Compound 1 (0.5 g, 5.21 mmol), adenosine (1.4 g, 5.24 mmol), and triethyl orthoformate (0.776 g, 5.24 mmol) were dissolved in 18 ml of DMF. Then the 4 M HCl in dioxane (4.08 ml) was added to the mixture. The reaction mixture was stirred at room temperature overnight. The reaction mixture was poured into diethyl ether (250 ml). Then the oil residue was dissolved in chloroform (100 ml) and the organic phase was washed once with sodium bicarbonate solution (2%) and then three times with water, and then dried over anhydrous MgSO$_4$. The solvent was removed via rotary evaporator. The crude product was purified by chromatography (chloroform:methanol=10:1). $^1$H NMR (CDCl$_3$) δ 8.32 (s, 1H), 7.85 (s, 1H), 7.27 (s, NH, 1H), 6.49 (d, J=10 Hz, 1H), 5.92 (d, J=5 Hz, 2H), 5.85 (s, NH$_2$, 2H), 5.24 (d, J=4 Hz, 2H), 5.23 (d, J=4 Hz, 2H), 4.54 (s, 1H), 3.99 (d, J=13 Hz, 1H), 4.82 (d, J=13 Hz, 1H), 2.47 (m, 2H), 2.15 (t, 2H), 2.03 (s, CH, 1H), 1.36 (s, 3H) ppm.

Example 15—Synthesis of Tert-butyl(6-(pro-2-yn-1-ylamino)hexyl)carbamate (Compound 2)

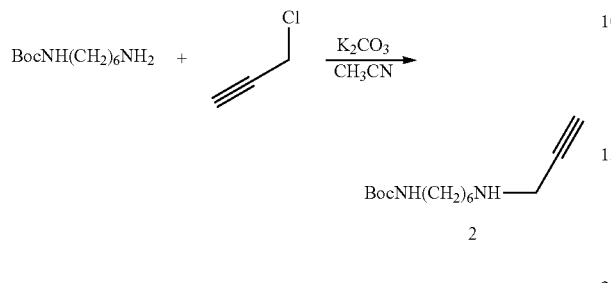

Propargyl chloride (344.4 mg, 4.6 mmol, 1 equiv.), Boc-protected amine (1.00 g, 4.62 mmol, 1 equiv.) was dissolved in acetonitrile, and anhydrous $K_2CO_3$ was added. The reaction was stirred at room temperature for 16 hours. Then, 100 ml of water and 100 ml of diethyl ether were added. The organic phase was separated and the aqueous phase extracted with diethyl ether (2×50.0 ml). The solvent was removed under reduced pressure. The crude product was purified by column chromatography on a basic alumina (DCM:MeOH=50:1). After drying on high-vacuum the product was obtained as a yellow oil (0.7991 g, 68%) yield. $^1$H NMR (CDCl$_3$) δ 4.5 (s, 1H, NH), 3.45 (s, 2H), 3.14 (d, 2H), 2.72 (m, 2H), 2.23 (s, 1H), 1.5 (s, 8H), 1.46 (s, 9H) ppm. LC-MSD-XCT (TCI) called for $C_{14}H_{26}N_2O_2$ [M]$^+$: 254.20; found 455.03

Example 16—Synthesis of Compound 3

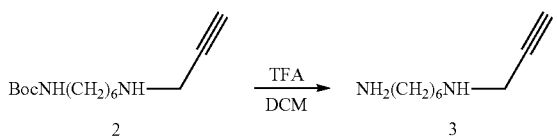

Compound 2 (514 mg, 2.0 mmol) was subjected to a solution of 10% TFA in DCM (15 ml) for 3 hours. The water was added and the organic phase was separated. Then the water phase was neutralized with 10% NaHCO$_3$ to pH 8.0. Then water was evaporated under reduced vacuum. The residue was washed with dichloromethane, the organic fractions were combined, and the dichloromethane was removed. The product was obtained as a yellow oil (300 mg, 96%). The crude product was used directly for next step. LC-MSD-XCT (TCI) called for $C_9H_{18}N_2$ [M]$^+$: 154.15; found 455.19.

Example 17—Synthesis of Adenosine-6-amine

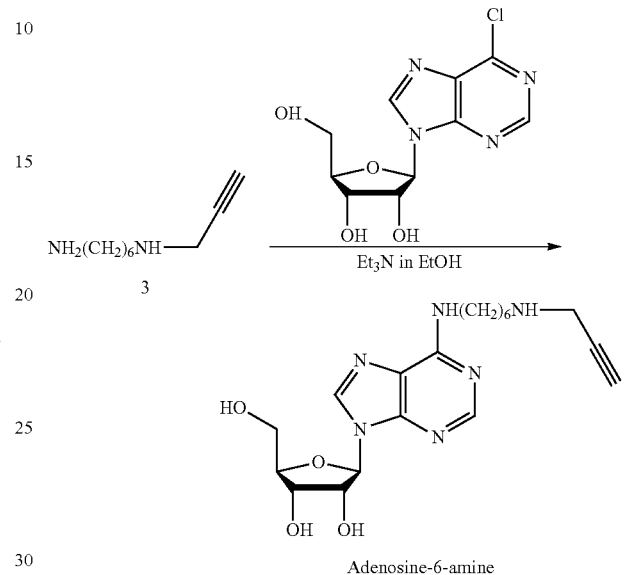

Adenosine-6-amine

A mixture of 6-chloro-9-(β-D-ribofuranosyl)purine (527 mg, 1.84 mmol), compound 3 (300 mg, 1.94 mmol), 1.84 mmol of Et$_3$N, and 25 ml of ethanol was refluxed at 60° C. for 18 hours (Bhattarai et al., "α,β-Methylene-ADP (AOPCP) Derivatives and Analogues: Development of Potent and Selective ecto-5'-Nucleotidase (CD73) Inhibitors," *J. Med. Chem.* 58:6248-6263 (2015), which is hereby incorporated by reference in its entirety). After completion of the reaction the solvent was evaporated under high vacuum. Purification was performed using silica gel chromatography (MeOH:DCM, 1:10) and the product was obtained as white solid (380 mg, 50%) yield. $^1$H NMR (DMSO-d$_6$) δ 9.03 (s, NH, 1H), 8.23 (s, 1H), 8.10 (s, 1H), 5.78 (d, J=8 Hz, 1H), 5.35 (d, J=4 Hz, 2H), 5.10 (d, J=4 Hz, 1H), 4.50 (m, 1H), 4.04 (m, J=4 Hz, 1H), 3.87 (t, 1H), 3.59 (dd, J=12 HZ, J=4 Hz, 1H), 3.49 (dd, J=12 Hz, J=4 Hz, 1H), 3.46 (s, 2H), 3.07 (m, 2H) 2.33 (t, 2H), 1.50 (m, 2H), 1.32 (s, 2H), 1.27 (m, 4H) ppm. LC-MSD-XCT (TCI) called for $C_9H_{18}N_2$ [M]$^+$: 504.21 Found: 404.21.

Example 18—Conjugation of Adenosine-6-amine to PLA-β-PEG-N$_3$ Copolymer

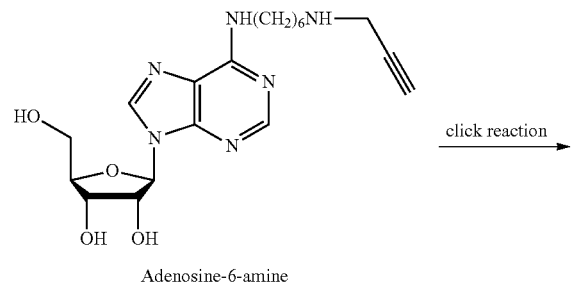

Adenosine-6-amine

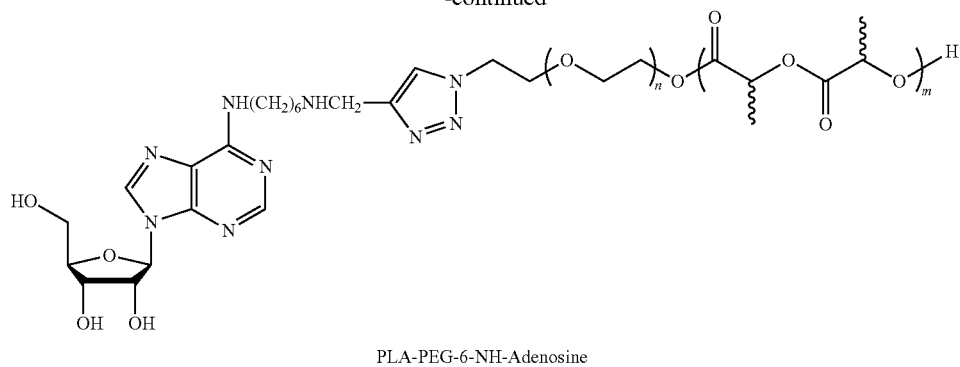

PLA-PEG-6-NH-Adenosine

PLA-PEG-6-NH-Adenosine was conjugated to PLA-b-PEG-N$_3$ according to the similar protocol as described in Example 6.

Example 19—Nanoparticle Formation

Nanoparticles were prepared using similar protocol to the one described in Example 26.

Example 20—Synthesis of Compound 5

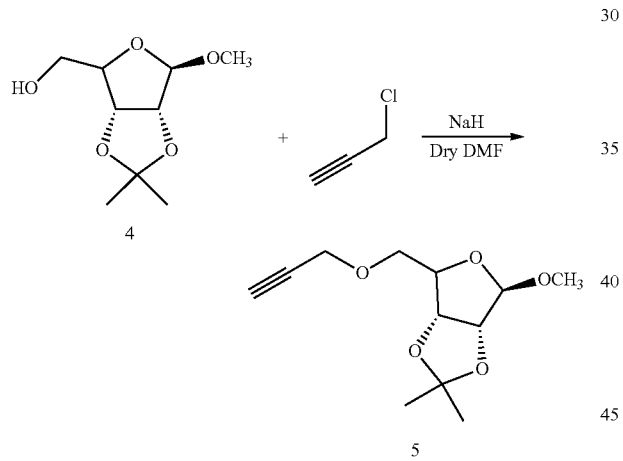

Methyl 2,3-O-isopropylidene-β-D-ribofuranoside (4; 4.0 g, 20 mmol) was dissolved in dry dimethylformamide (DMF; 30 ml) (van Tilburg et al., "5'-O-Alkyl Ethers of N,2-Substituted Adenosine Derivatives: Partial Agonists for the Adenosine A1 and A3 Receptors," *J. Med. Chem.* 44:2966-2975 (2001), which is hereby incorporated by reference in its entirety). The mixture was cooled (0° C.), and NaH (60% in mineral oil, 1.78 g, 23 mmol) was slowly added. The mixture was allowed to warm to room temperature and cooled again, and propargyl chloride (0.31 mol) was added very slowly. The mixture was stirred at room temperature overnight. The mixture was treated with methanol (10 ml) and concentrated in vacuum. It was coevaporated with toluene (2×10 ml). The (black) mixture was extracted with water and EtOAc (25 ml each). The water layer was subsequently extracted with CH$_2$Cl$_2$. The organic layers were combined, dried (MgSO$_4$), and concentrated. The residue was purified by column chromatography (Eluent 10% MeOH in EtOAc): yield 0.9 g (12.5 mmol, 62%).

Example 21—Synthesis of Compound 6

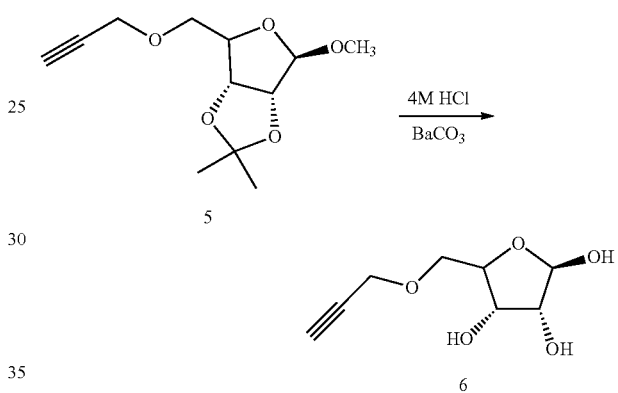

The Methyl 5-O-propargyl-2,3-O-isopropylidene-β-D-ribofuranose (3 g, 12.5 mmol) was dissolved in 60 ml of HCl (0.04 M) and was refluxed for 2 hours (van Tilburg et al., "5'-O-Alkyl Ethers of N,2-Substituted Adenosine Derivatives: Partial Agonists for the Adenosine A1 and A3 Receptors," *J. Med. Chem.* 44:2966-2975 (2001), which is hereby incorporated by reference in its entirety). The solution was neutralized with BaCO$_3$, filtered, and concentrated. The mixture was purified by column chromatography (Eluent 10% MeOH in EtOAc): yield 3 g (4.7 mmol, 38%).

Example 22—Synthesis of Compound 7

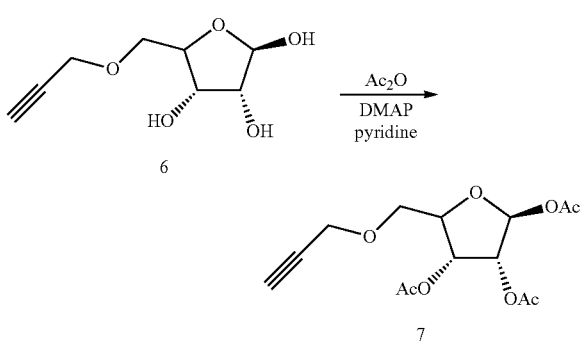

The 5-O-propargayl-R,β-D-ribofuranose (4.7 mmol) was dissolved in 50 ml of pyridine (van Tilburg et al., "5'-O-Alkyl Ethers of N,2-Substituted Adenosine Derivatives: Partial Agonists for the Adenosine A1 and A3 Receptors," *J. Med. Chem.* 44:2966-2975 (2001), which is hereby incorporated by reference in its entirety). A catalytic amount of (dimethylamino)pyridine (DMAP) (60 mg, 0.47 mmol) and acetic anhydride (1.2 g, 11.75 mmol) were added. The mixture was stirred for 2 hours at room temperature, concentrated in vacuum, and coevaporated with toluene. The oil was extracted with water and EtOAc (25 ml each). The organic layer was dried (MgSO₄), concentrated, and purified by column chromatography (Eluent: EtOAc): yield 1.09 g (3.5 mmol, 74%). ¹H NMR (CDCl₃) δ 6.16 (s, 1H), 5.43 (m, 1H), 5.36 (m, 1H), 4.39 (m, 1H), 4.31 (s, 2H), 3.72 (dd, 2H), 2.45 (s, 1H), 2.11 (3×s, 9H) ppm.

Example 23—The Procedure for the Coupling of Compounds 7 to 6-Chloropurine to Give Compounds 8 subsequently dissolved in 75 ml of dry 1,2-dichloroethane. The solution was gently refluxed, and after 5 min TMS triflate (0.5 ml, 2.58 mmol) was added. The mixture was refluxed for 2 hours, cooled to room temperature, and diluted with CH₂Cl₂. It was then extracted with 5% NaHCO₃ and water. The organic layer was dried (MgSO₄), concentrated, and 6-Chloro-9-(2,3-di-O-acetyl-5-O-propargyl-β-D-ribofuranosyl)purine (8) was purified by column chromatography (eluent 3% acetone in DMC) yield: (700 mg, 49%). ¹H NMR (CDCl₃) δ 8.80 (d, 1H), 8.73 (d, 1H), 5.83 (d, J=5 Hz, 1H), 5.62 (d, J=5 Hz, 1H), 5.34 (dd, J=5 Hz, 1H), 4.46 (s, 1H), 4.33 (m, 2H), 3.59 (dd, 2H), 2.56 (s, 1H), 2.05 (3×s, 9H) ppm.

Example 24—Synthesis of 5-O-Propargyl-adenosine

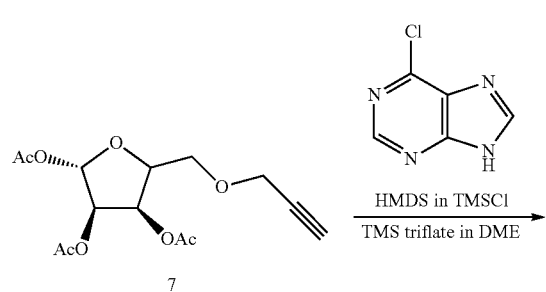

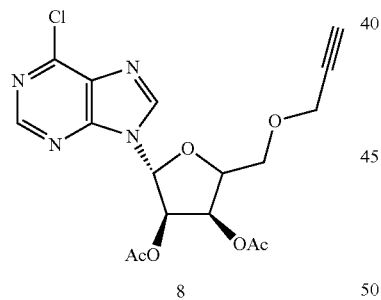

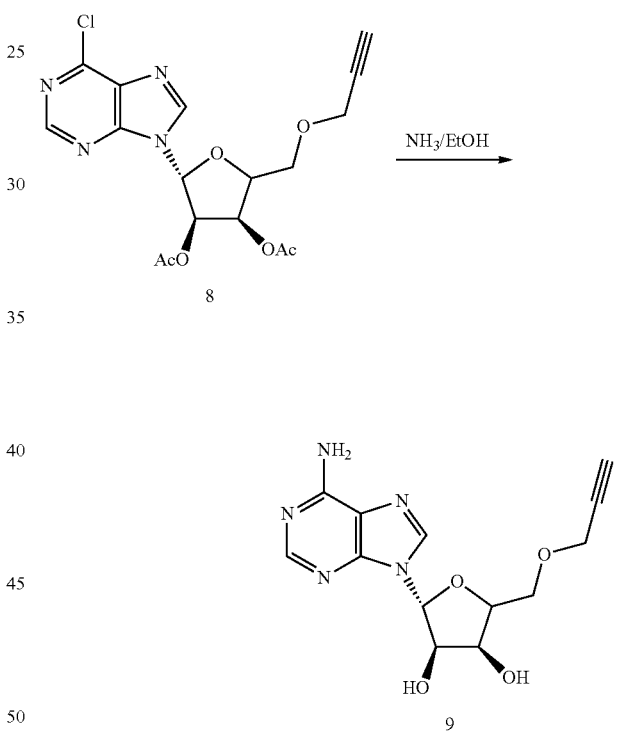

Silylation of the Base

6-Chloropurine (770 mg, 5 mmol) was treated with 1,1,1,3,3,3-hexamethyldisilazane (HMDS; 20 ml, 93.1 mmol) and 50 μL of chlorotrimethylsilane (TMSCl; 0.4 mmol) at 130° C. for 20 hours (van Tilburg et al., "5'-O-Alkyl Ethers of N,2-Substituted Adenosine Derivatives: Partial Agonists for the Adenosine A1 and A3 Receptors," *J. Med. Chem.* 44:2966-2975 (2001), which is hereby incorporated by reference in its entirety). The silylated compound was concentrated and used without further purification.

Vorbruggen Coupling

To the silylated base (5 mmol) was added compound 7 (3.5 mmol) in 7.5 ml of dry 1,2-dichloroethane. The residue was coevaporated twice with dry 1,2-dichloroethane and The compound 8 (700 mg, 1.71 mmol) was dissolved in 4% NH₃/EtOH (30 ml), and the mixture was stirred overnight at room temperature (van Tilburg et al., "5'-O-Alkyl Ethers of N,2-Substituted Adenosine Derivatives: Partial Agonists for the Adenosine A1 and A3 Receptors," *J. Med. Chem.* 44:2966-2975 (2001), which is hereby incorporated by reference in its entirety). The mixture was concentrated and purified by column chromatography (Eluent 10% methanol in DMC) yield: (300 mg, 58%). ¹H NMR (CDCl₃) δ 8.72 (s, 1H), 8.59 (s, 1H), 6.16 (d, J=5 Hz, 1H), 4.70 (s, NH, 1H), 4.62 (d, J=5 Hz, 1H), 4.50 (d, J=5 Hz, 1H), 4.49 (d, J=5 Hz, 1H), 4.22 (s, 2H), 3.90 (d, J=10 Hz, 1H), 3.79 (d, J=10 Hz, 1H), 2.49 (s, 1H), 2.05 (3×s, 9H) ppm.

Example 25—Conjugation of Alkynated Terminated Adenosine to PLA-β-PEG-N₃ Copolymer

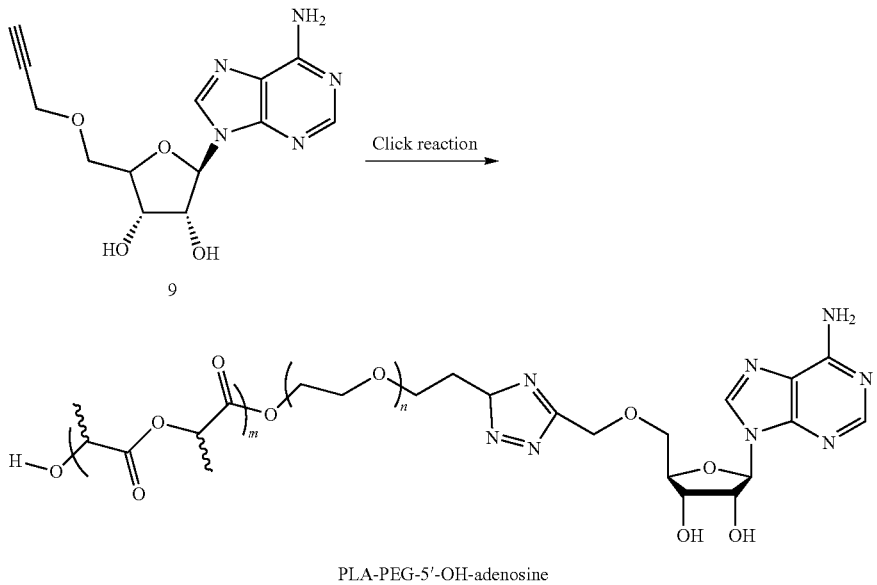

PLA-PEG-5'-OH-adenosine

A representative synthesis (PLA-β-PEG400-N₃) was as follows. To a degassed solution of PLA-b-PEG-N₃ (200 mg, 10 μmol, 1 equiv) and alkyne adenosine (18 equiv) in anhydrous DMF (12 ml) was added with a syringe, a degassed solution of CuBr (10 mg, 69 μmol, 6.9 equiv) and PMDETA (37 μL, 0.179 mmol, 17 equiv) in anhydrous DMF (800 μL). The reaction mixture was stirred for 16 hours at 65° C. under nitrogen. The solution was concentrated under reduced pressure and the residue was dissolved into chloroform, then washed with saline solution and water until the organic phase became colorless. Then the organic phase was dried by anhydrous sodium sulfate and removed by rotary evaporation. The residue was dissolved in minimum amount of THF, and further precipitate in water for third times. The precipitate was freeze-dried to yield a white powder. See Mackiewicz et al., "Precise Engineering of Multifunctional PEGylated Polyester Nanoparticles for Cancer Cell Targeting and Imaging," Chem. Mater. 26: 1834-1847 (2014), which is hereby incorporated by reference in its entirety.

Example 26—Nanoparticle Formation

The copolymer attached with adenosine (30 mg in total) was dissolved in ethyl acetate (1.2 ml). The above organic phase was added to 3.3 ml of an aqueous phase containing 1% w/v Pluronic F68. The mixture was then vigorously shaken using a vortex shaker for 1 min. The resulting emulsion was ultrasonicated (using an ultrasonic probe) for 3 min and the organic solvent was removed under reduced pressure using a rotary evaporator. The resulting nanoparticle suspension was ultracentrifuged at 1600 g for 45 min and the pellet was resuspended in 3 ml of pH=7.4 PBS. The nanoparticles were filtered through a 1 μm glass filter first and then 0.45 μm and stored at 4° C. until use.

Example 27—Analytical Techniques

NMR Spectroscopy

NMR spectroscopy was performed in CDCl₃ or DMSO-d₆. ¹H NMR spectroscopy was performed on a Bruker Avance 500 spectrometer at 500 MHz (¹H).

Concentration of Nanoparticles

Figure 8:
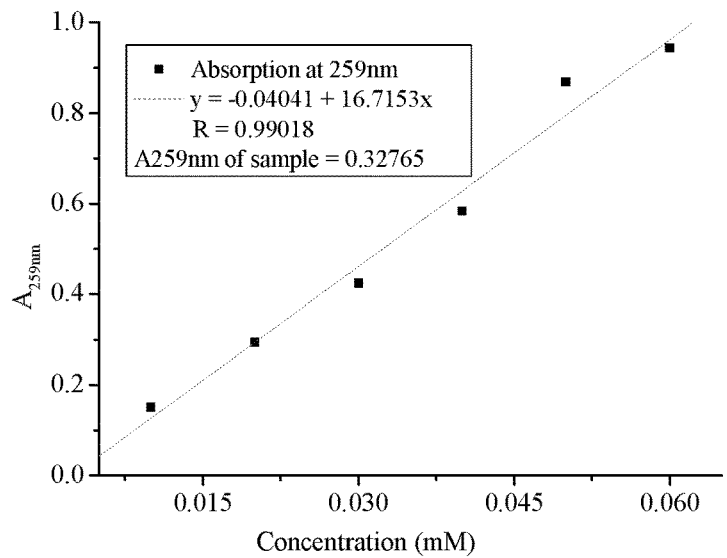
FIG. 8 is a graph showing the best-fit line of the standard solution of adenosine.

Based on the Beer's Law, the various standard solution of adenosine were made and being quantified through calorimetric assays. Then the data was graphed based on the concentrations and a Best-Fit line was gained through the points. (See FIG. 8). From the slope of the best-fit line together with the absorbance, the concentration of nanoparticles was calculated.

Dynamic Light Scattering (DLS)

Measurement of the nanoparticle diameter was performed using a Delso™ Nano from Beckman counter under 90° scattering angles at 20° C. (Table 1).

TABLE 1

| | Diameter Size (nm) | Concentration |
|---|---|---|
| PLA-PEG400-3',4'-OH-adenosine | Around 150 | 0.017 mM |
| PLA-PEG400-6-NH-adenosine | Around 160 | 0.011 mM |
| PLA-PEG400-5'-OH-adenosine | Around 153 | 0.021 mM |
| MeOPEG550-PLA | Around 138 | — |
| PLA-PEG2000-3',4'-OH-adenosine | Around 110 | 0.16 mM |
| PLA-PEG2000-6-NH-adenosine | Around 130 | 0.12 mM |
| PLA-PEG2000-5'-OH-adenosine | Around 130 | 0.19 mM |

Figure 13:
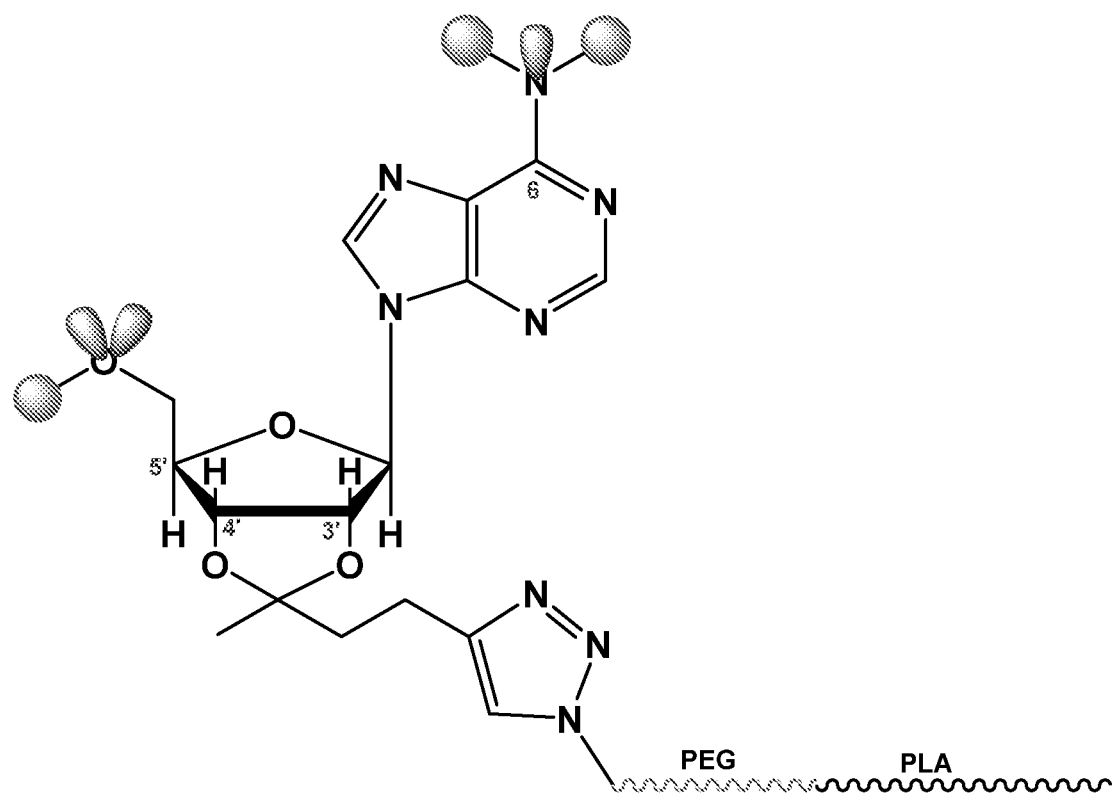
FIG. 13 is a schematic showing PLA-PEG copolymer attachment through the 3',4'-OH groups of the sugar.

A unique and surprising feature of the PLA-PEG copolymer attachment through the 3',4'-OH groups results from the fact that the molecular recognition event between the adenosine and adenosine receptor (which lead to the activation of the latter, resulting in fibronectin formation) requires multiple H-bonding, and these are possible when both the amine and the 5'-OH participate. In FIG. 13, the 5'-OH is shown with both the Fe proton (sphere), which is H-bond donor, and the two lone pairs (shown as orbitals) which are H-bond receptors. Similarly, in the amine, the two hydrogens (shown as spheres) and electron pair are shown. Without wishing to be bound by theory, if the formation of multiple H-bonding events between the adenosine and the receptor requires both in vivo (i.e., the amine and the 5'-OH), the only reactive nanoparticles will be those where the polymer had been attached through the 3' and 4'-OH groups, which indeed has been observed in multiple in vitro and experiments.

Example 28—Prophetic—Preparation of Adenosine-Functionalized Nanoparticles of Different Sizes To study of efficacy of adenosine-functionalized biodegradable with different core sizes, the PEG-N$_3$ and lactide stoichiometry shall be changed, with the aim of creating 3 different particle sizes, all using PEG-N$_3$ with molecular weight of 2000. All particles will be prepared with, and without adenosine. All nanoparticle sizes will be determined using light scattering.

Example 29—In Vitro Testing of PLA-b-PEG-Adenosine Nanoparticles

Figures 4A, 4B:
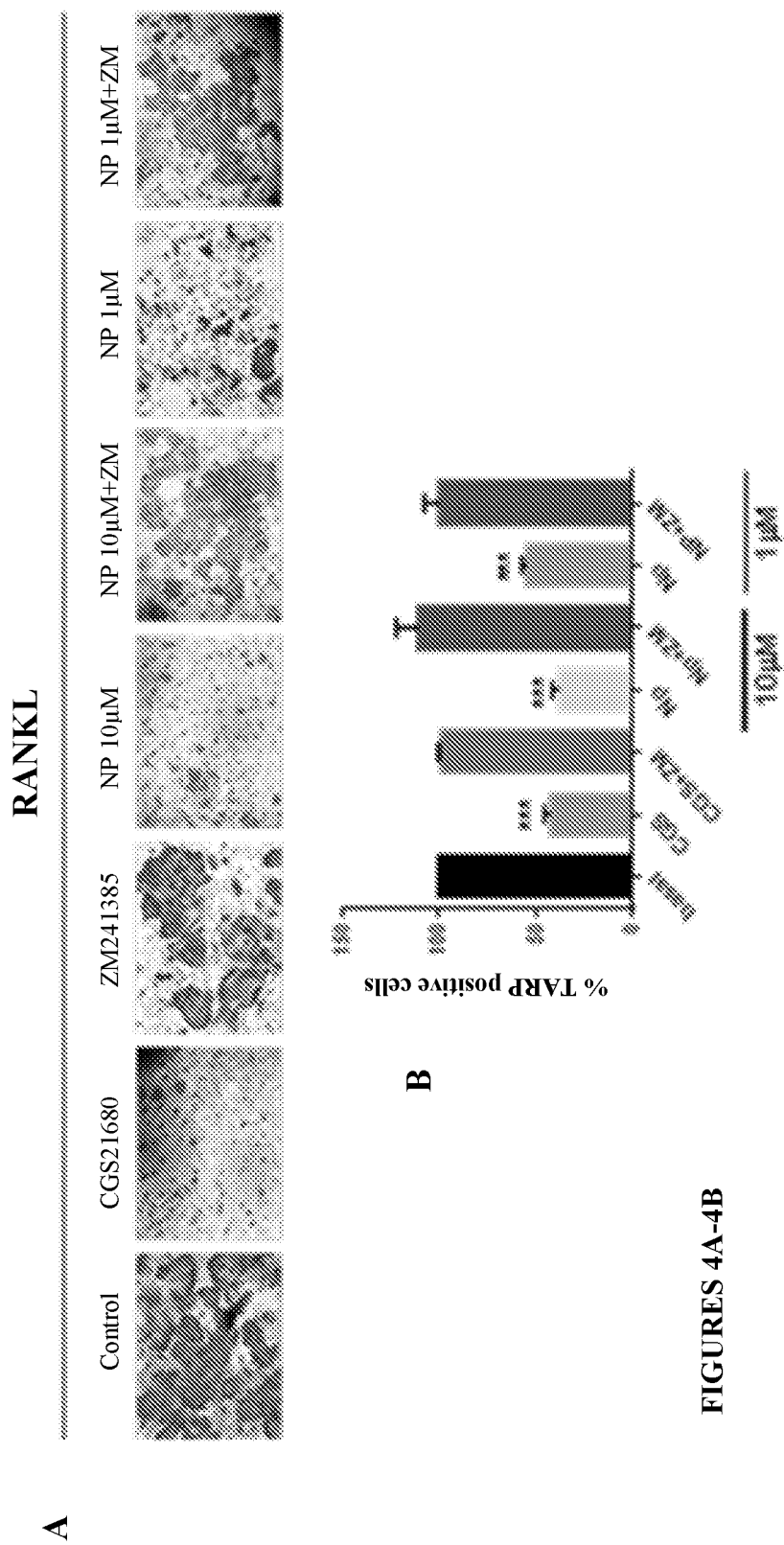
FIGS. 4A-4B show results demonstrating that nanoparticles of the present invention block Receptor Activator of NKκB Ligand (RANKL)-induced osteoclast differentiation. 5000 RAW264.7 cells were plated, treated with 50 ng/ml RANKL, challenged with $10^{-6}$M CGS21680 (A2AR agonist) and nanoparticles containing Adenosine (NP) at doses 10 μM and 1 μM alone or in the presence of $10^{-6}$M ZM241385 (A2AR antagonist), and cultured for four days. Tartrate-resistant acid phosphatase (TRAP) staining was carried out. The images of the stained samples are shown in FIG. 4A. The number of TRAP-positive MNCs containing ≥3 nuclei/cell was scored.

All suspensions were subject to filter sterilization through 22μ filters prior to usage and then stored at 4° C. until use. The effect of PEG2000-adenosine conjugate nanoparticles (see Example 7) was tested in three separate assays for their capacity to activate adenosine receptors. As shown in FIGS. 3A-3D, culture of primary human dermal fibroblasts with the nanoparticle-adenosine conjugates stimulated an increase in Collagen I (FIG. 3A (Western Blot image) and FIG. 3B (graph of quantified results)) and Collagen III (FIG. 3C (Western Blot image) and FIG. 3D (graph of quantified results)) production compared to control (basal), as previously reported for agents that ligate A2A adenosine receptors. Moreover, in these studies an adenosine A2A receptor antagonist completely blocked the effect of the nanoparticles on collagen I and collagen III production. FIG. 4 shows that, like the A2A adenosine receptor agonist CGS21680, the nanoparticles block RANKL-induced osteoclast differentiation and the effects of both CGS21680 and the nanoparticles (at two different concentrations).

To determine whether the adenosine-conjugated nanoparticles stimulate adenosine receptors, the effect of nanoparticles alone, adenosine, or the three types of adenosine-conjugated nanoparticles (i.e., PLA-PEG-3',4'-OH-adenosine, PLA-b-PEG-6-NH-adenosine, and PLA-b-PEG-5'-OH-adenosine) to stimulate cAMP accumulation was tested. The compounds tested were as follows:

"Ade PEG 2000 ketal" (referred to in FIG. 9 as "Ade PEG 2000")—PLA nanoparticles conjugated to PEG 2000, which is conjugated to adenosine on the 3', 4' hydroxyl groups on the ribose (see FIG. 13; also referred to as, e.g., PLA-PEG2000-3',4'-OH-adenosine and PEG 2000 PLA-ketal);

"PEG400 PLA amine"—PLA nanoparticles conjugated to PEG 400, which is conjugated to the NH group on the adenosine purine (also referred to as, e.g., PLA-PEG400-6-NH-adenosine);

"PEG 400 PLA ketal"—PLA nanoparticles conjugated to PEG 400, which is conjugated to adenosine on the 3',4'-hydroxyl groups on the ribose (also referred to as, e.g., PLA-PEG400-3',4'-0H-adenosine);

"New ADE PEG 400 PLA"—PLA nanoparticles conjugated to PEG 400, which is conjugated to the NH 5'-OH group on the ribose (also referred to as, e.g., PLA-PEG400-5'-OH-adenosine);

"PEG 2000 PLA new ade"—PLA nanoparticles conjugated to PEG 2000, which is conjugated to the NH 5'-OH group on the ribose (also referred to as, e.g., PLA-PEG2000-5'-OH-adenosine); and "PEG 2000 PLA-amine"—PLA nanoparticles conjugated to PEG 2000, which is conjugated to the NH group on the adenosine purine (also referred to as PLA-PEG2000-6-NH-adenosine).

Figure 5:
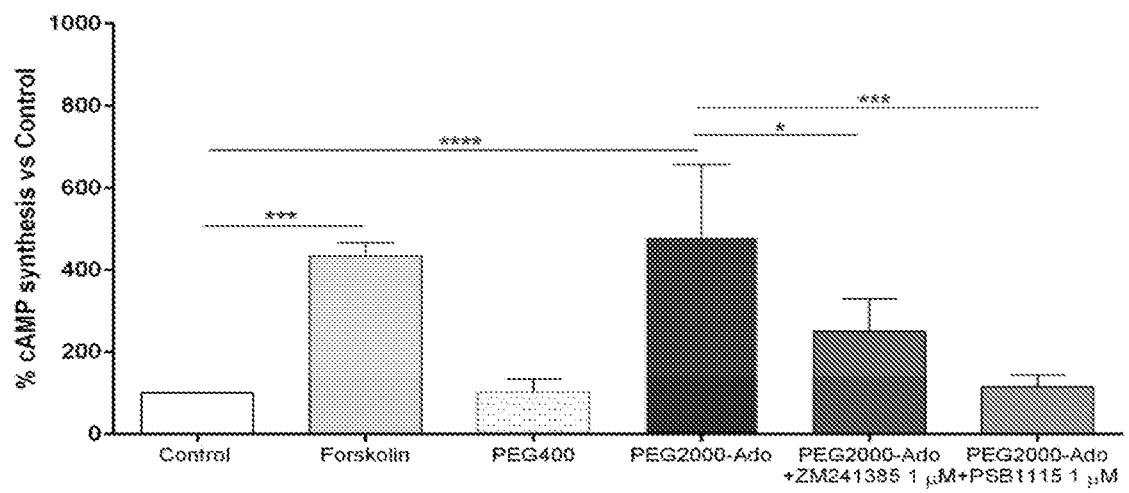
FIG. 5 is a bar graph of results showing cyclic adenosine monophosphate (cAMP) synthesis in RAW cells. Stimulation of RAW264.7 cells with the compound PEG2000-Ado (i.e., PLA-PEG-3,4-OH-adenosine (which may also be referred to as PLA-PEG-3',4'-OH-adenosine and which is referred to in the in vivo and in vitro experiments set forth herein as PEG2000-Ado; Ade PEG 2000; PEG2000 Ade; PEG2000-adenosine conjugate; adenosine-conjugated PEG2000 nanoparticles; and the like)) (approximately 10 μM, 5 min) induced an increase in cAMP production (400% compared to the control condition), reversed by the co-administration of ZM241385 1 μM (antagonist for A2A adenosine receptors) and PSB1115 1 μM (antagonist for A2B adenosine receptors). Forskolin, an activator of adenylate cyclase, was administered at 100 nM as an internal control. These results show that adenosine-conjugated particles stimulate cAMP accumulation in RAW264.7 cells via both the A2A and A2B adenosine receptors.
Figures 6A, 6B:
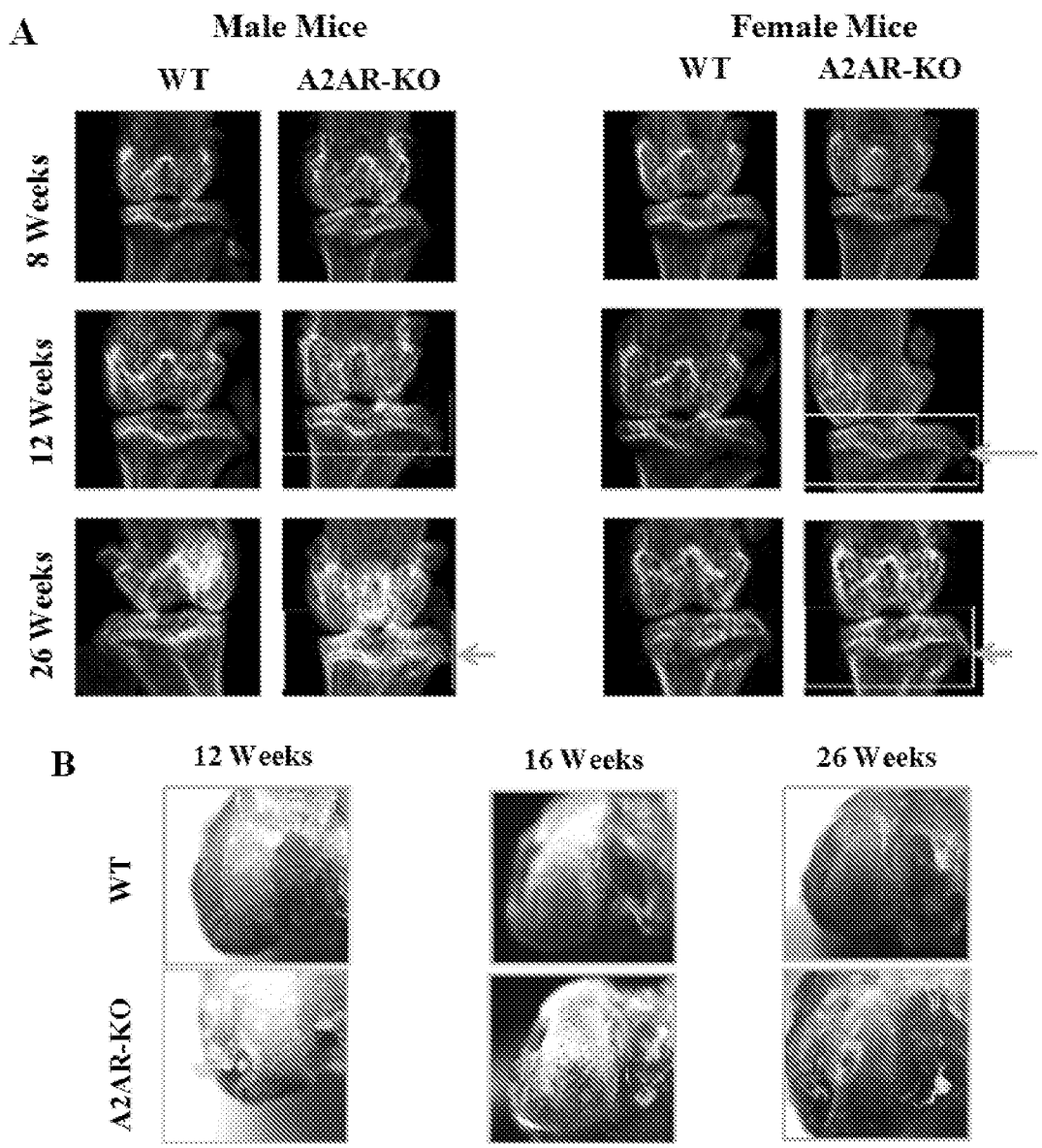
FIGS. 6A-6B show the alteration of knee surfaces in A2A receptor knockout (A2AR KO) mice.
Figures 7A, 7B:
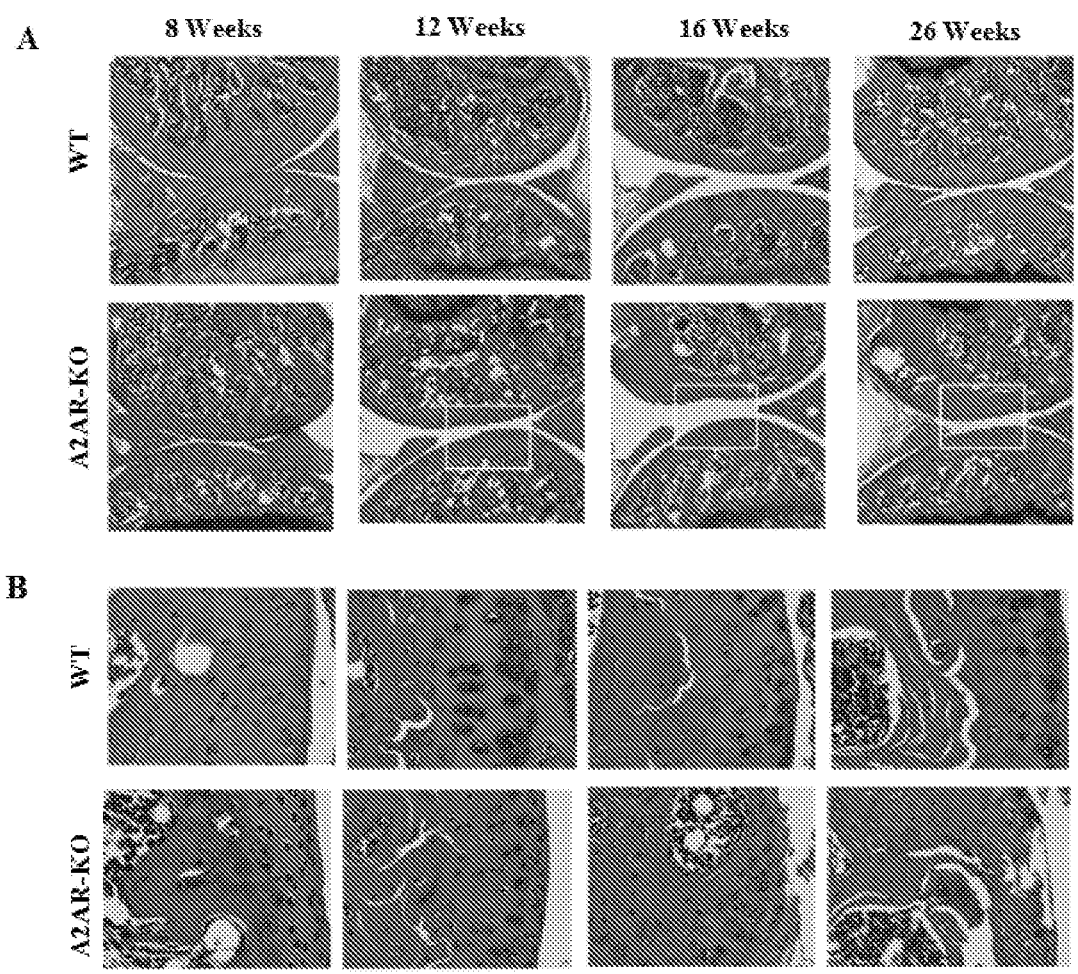
FIGS. 7A-7B are photomicrographs of knee joints in WT and A2AR KO mice at 8 weeks, 12 weeks, 16 weeks, and 26 weeks of age which show histomorphology of the knee joint (H & E staining).
Figure 9:
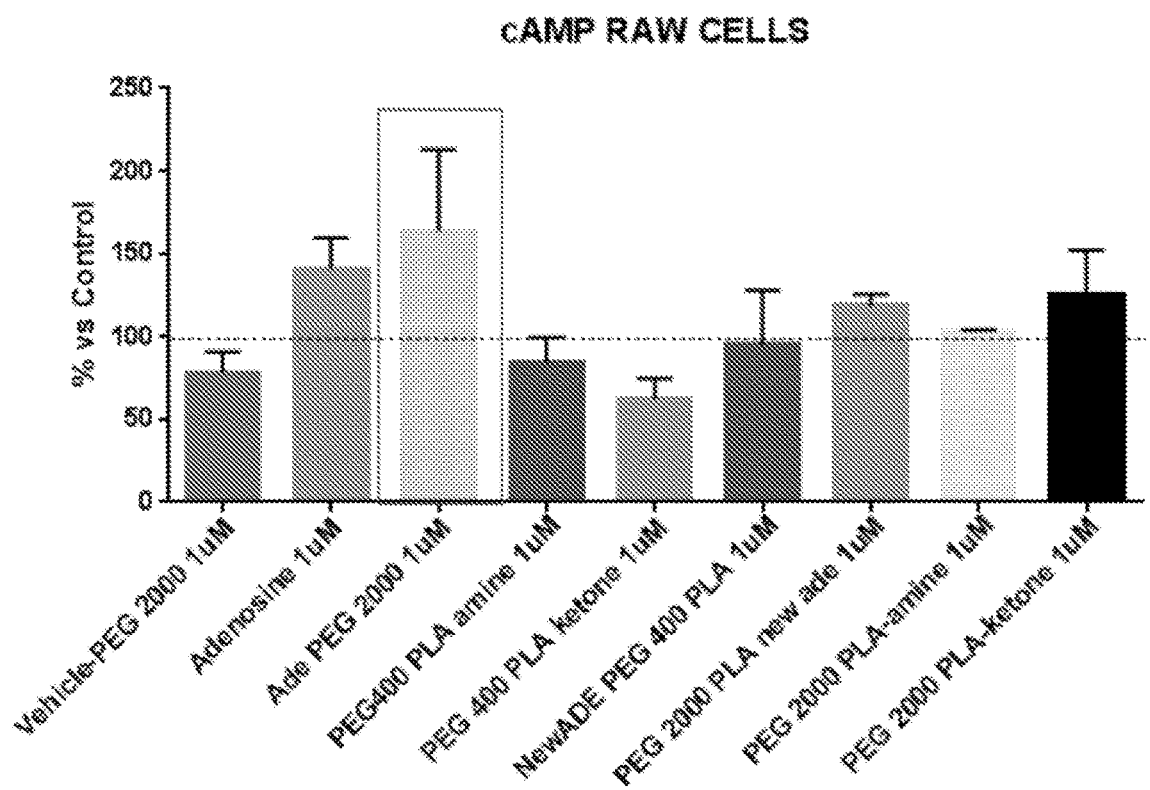
FIG. 9 is a graph showing cAMP synthesis in RAW cells stimulated by multiple particles conjugated to adenosine.

As shown in FIG. 9, incubation of RAW264.7 cells with the agents demonstrates that the nanoparticles conjugated to adenosine on the 3', 4' hydroxyl groups on the ribose (i.e., Ade PEG 2000, see Example 7) as the only particle to stimulate a significant increase in cAMP accumulation. None of the nanoparticles conjugated to the PLA nanoparticles through the lower molecular weight PEG (PEG400) had any effect on cAMP, and the 5'-OH and amine-conjugated constructs (PLA-PEG-5'-OH adenosine, and adenosine 6-amine, respectively) similarly had no significant effect on cAMP content. The adenosine-conjugated nanoparticles stimulated cAMP accumulation via both A2A and A2B adenosine receptors since co-incubation with selective antagonists for both A2A receptor (ZM241385) and A2B receptor (PSB1115) blocked the effect of the adenosine nanoparticles on cAMP accumulation (FIG. 5).

Figures 10A, 10B, 10C:
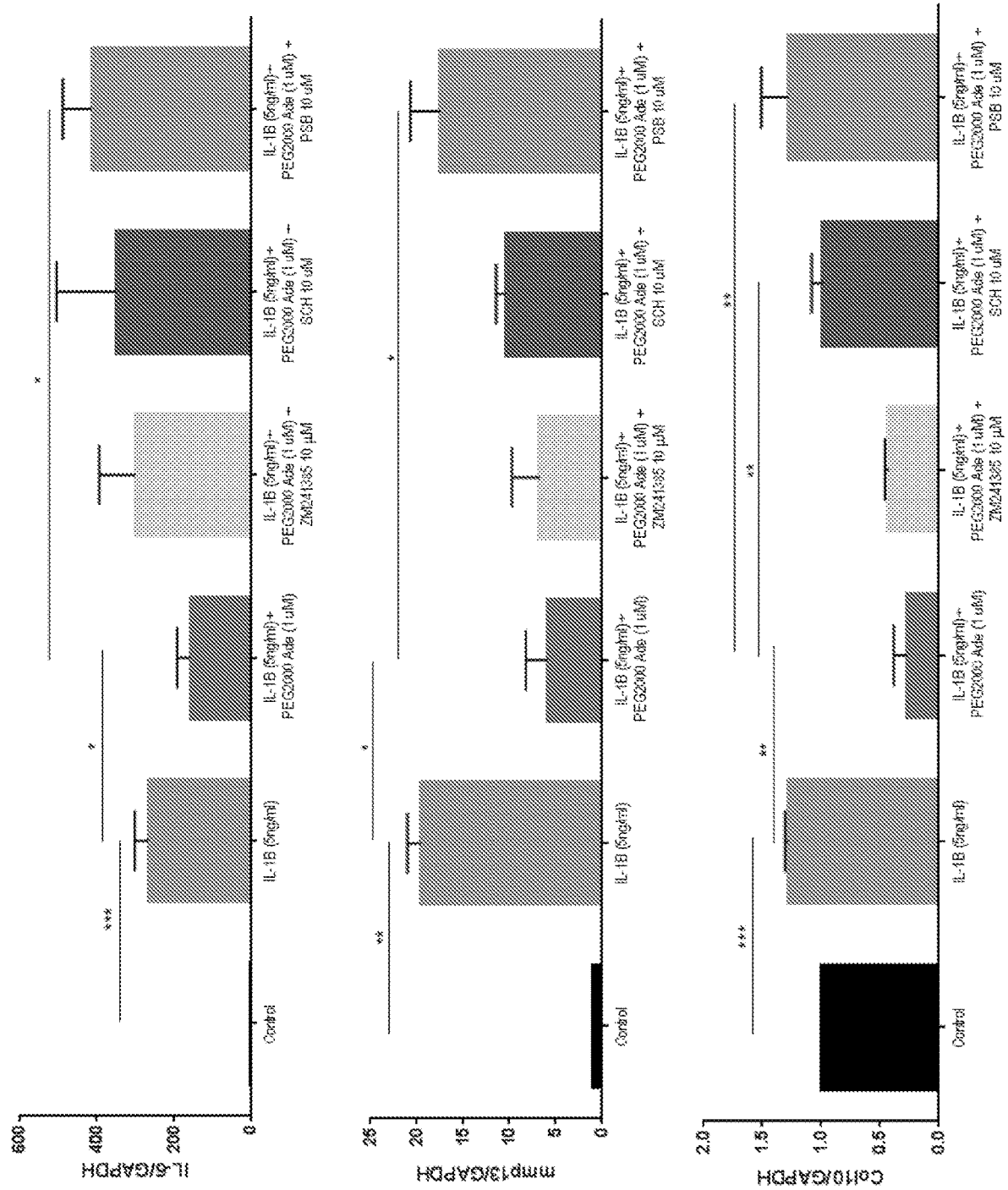
FIGS. 10A-10D are graphs showing experimental results obtained from WT primary chondrocytes following 24 hours of treatment.
Figure 10D:
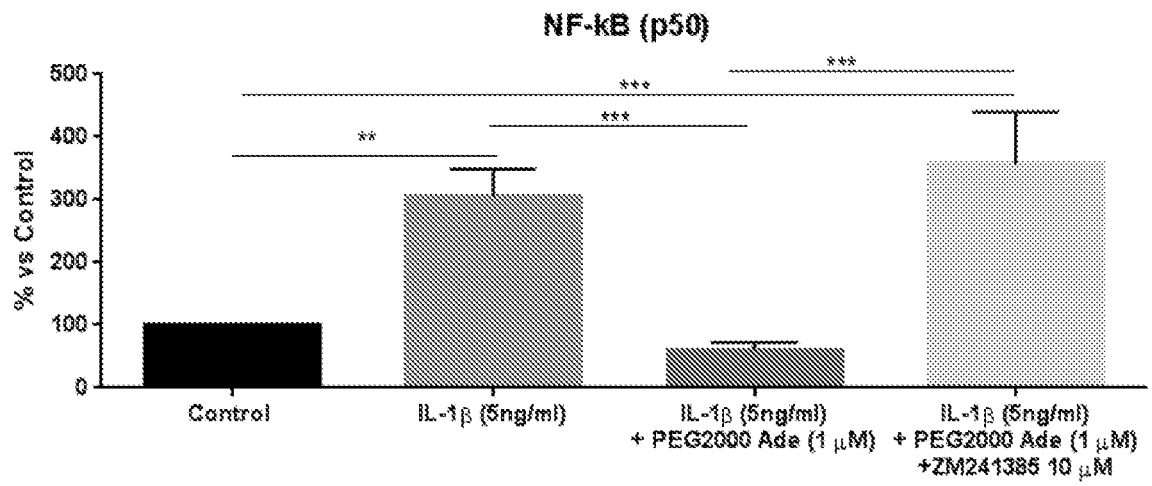

Similarly, the adenosine-conjugated nanoparticles inhibited the IL-1beta-stimulated expression of IL-6 by approximately 50%, an effect that was completely reversed by A2AR and A2BR antagonists (FIG. 10A). As shown in FIGS. 4 10B-10C, the adenosine-conjugated nanoparticles inhibited IL-1beta-stimulated MMP13 and Collagen 10 expression via stimulation of A2BR since the effect was reversed by the selective A2B antagonist but not by the A2AR-selective antagonists (FIGS. 4 10B-10C). In contrast, the adenosine-conjugated nanoparticles inhibited IL-1beta stimulated activation of NFkappab (FIG. 10D).

As described in the Examples above, PLA-PEG nanoparticles to which adenosine was covalently bound were prepared. These particles clearly activated A2AR and A2BR in appropriate cell types on the basis of inhibition of stimulation by selective A2AR or A2BR antagonists.

Example 30—Adenosine A2AR Knockout Mice

Adenosine A2AR knockout mice have gait disturbances with resulting abnormalities in movement, and movement analysis suggests that these mice suffer from pain in their joints. Histologic and radiologic analysis of the knees of these animals demonstrates that A2AR knockout mice suffer from severe osteoarthritis (FIGS. 6A-6B and 7A-7B). In addition, A2AR stimulation inhibits cytokine-induced chondrocyte production of inflammatory mediators associated with cartilage degeneration and chondrocyte hypertrophy.

Example 31—Induction of Post-Traumatic Osteoarthritis (PTOA) in Rats and Treatment with Adenosine in a Liposome Formulation The PTOA model is a non-invasive method for inducing anterior cruciate ligament (ACL) rupture in rat knees in vivo with a single load of tibia compression overload. See Ramme et al., "A Novel Rat Model for Subchondral Microdamage in Acute Knee Injury: A Potential Mechanism In Post-Traumatic Osteoarthritis," *Osteoarthritis Cartilage* 24(10): 1776-85 (2016), which is hereby incorporated by reference in its entirety.

For tibial loading, animals are anesthetized and maintained on 1-3% isoflurane. The left hindlimb is positioned between two loading platens: an upper platen that holds the flexed ankle at approximately 30 degrees of dorsiflexion and a lower platen that holds the flexed knee. The platens are aligned vertically in an electromagnetic materials testing machine (Bose ElectroForce 3200, Eden Prairie, Minn.). A preload of 1 N is applied to the knee before a single dynamic axial compressive load is applied.

Rats are treated with a nanoparticle conjugated to adenosine (100 µl), or with unconjugated nanoparticles or with saline for 8 weeks (6 animals for each group). The animals are separated into two main cohorts, the prevention group receiving the injection right after the ACL rupture and the treatment group receiving the first injection after 7 days. The injections are performed every 10 days. Prior to intraarticular (IA) injection the site is prepared aseptically for injection. The site is defined by palpating patella externally, and then injecting 100 µl of solution through the patellar ligament into the joint space. In some cases, the nanoparticles will be injected with a selective adenosine A2AR (ZM241385 or SCH58261) antagonist (10 µM), an A2BR antagonist (MRS1754), or an A3R (MRS1191) antagonist (10 µM).

After injury, rats are given a subcutaneous injection of buprenorphine (0.1 mg/kg body weight) for analgesia. After loading, animals are returned to normal cage activity. At the end point, the blood is collected by a cardiac puncture and both legs are harvested for histochemical (Trichrome, safranin O, H&E, PAS), immunohistochemical (collagen X, MMP13, osteopontin, fibronectin), and micro-computed tomography analysis in order to evaluate the alterations in bone and cartilage features. Histologic changes of osteoarthritis will be scored using OARSI criteria (Bridges et al., "N6-(2,2-diphenylethyl)adenosine, a novel adenosine receptor agonist with antipsychotic-like activity," *J. Med. Chem.*, 30: 1709-11 (1987), which is hereby incorporated by reference in its entirety).

Figure 11A:
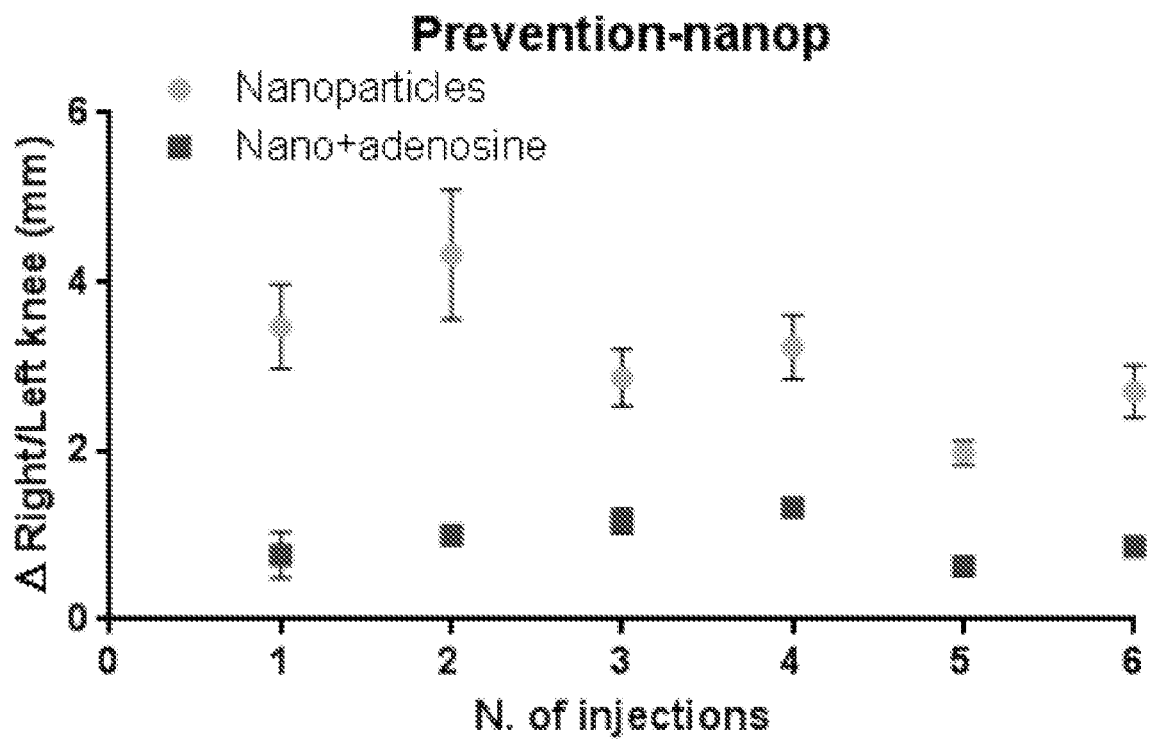
FIGS. 11A-11B are graphs showing experimental results demonstrating intra-articular injection of adenosine-conjugated nanoparticles diminishes knee swelling (FIG. 11A) and has no effect on rat weight (FIG. 11B) in a rat post-traumatic osteoarthritis model.
Figure 11B:
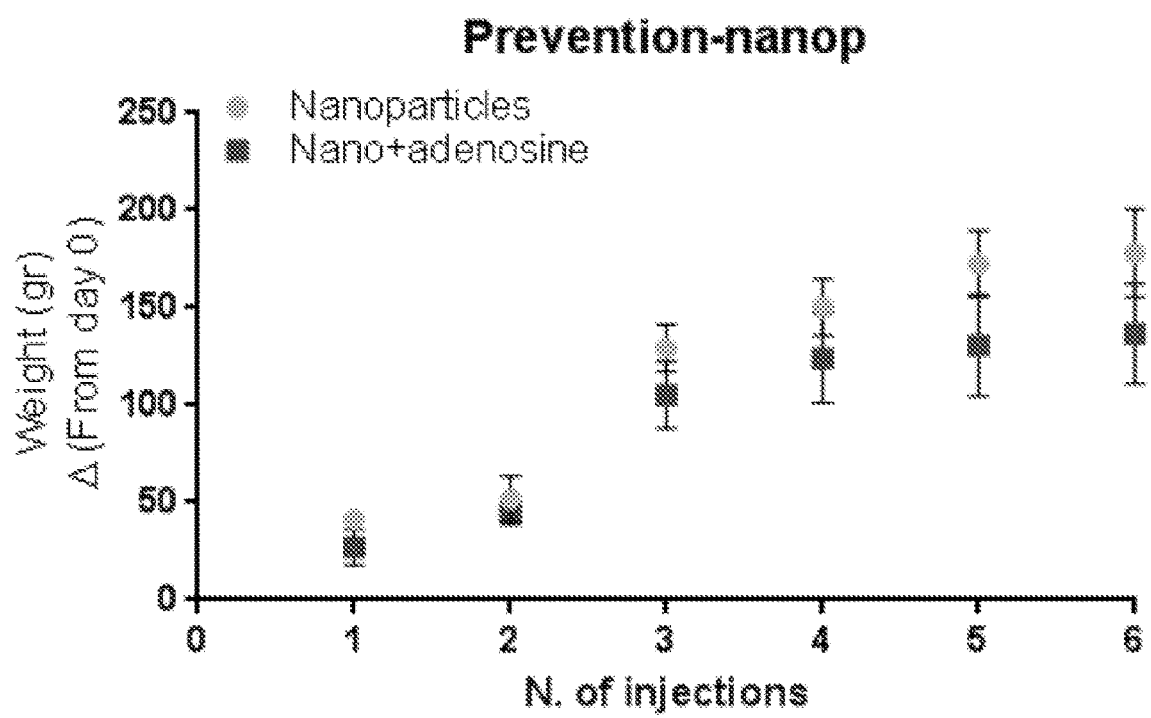
Figure 12A:
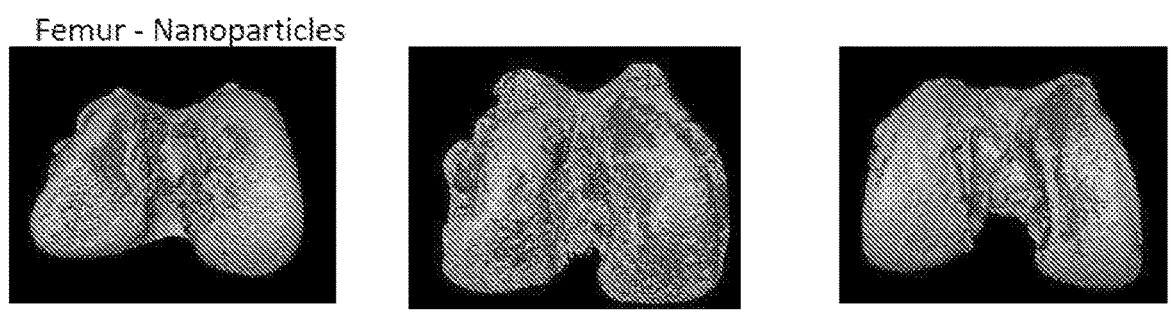
FIGS. 12A-12E show experimental results demonstrating that adenosine-conjugated nanoparticles preserve articular cartilage in a rat model of post traumatic osteoarthritis. Adenosine-conjugated nanoparticles prevented loss of cartilage tissue (see microcomputed tomography (microCT or μCT) images in FIGS. 12A (femur) and 12D (tibia)) compared to unconjugated nanoparticles (see microCT images in FIGS. 12B (femur) and 12E (tibia)).
Figure 12B:
Figure 12C:
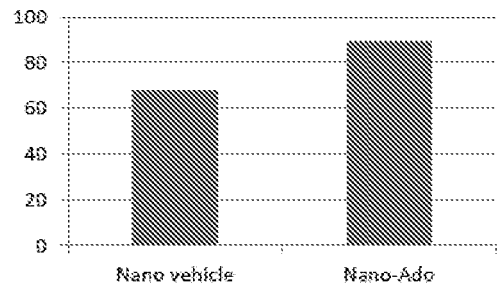
Figure 12D:
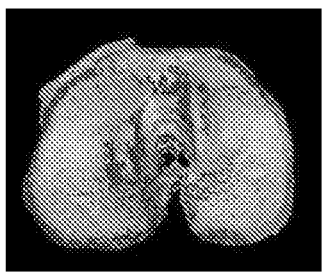
Figure 12D:
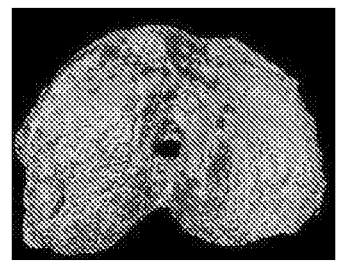
Figure 12D:
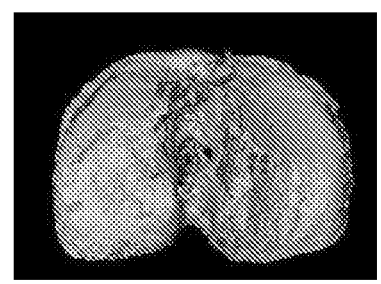
Figure 12E:
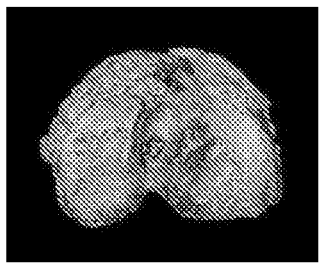
Figure 12E:
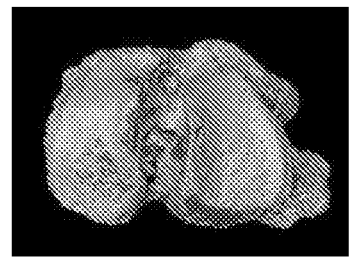
Figure 12E:
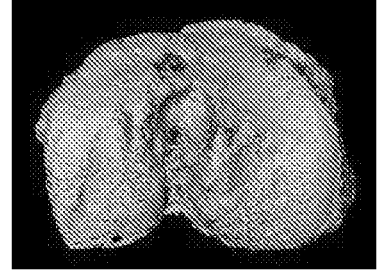

In preliminary studies using the above rat model of osteoarthritis in which the anterior cruciate ligament (ACL) is ruptured by compression, it has been found that intra-articular injection of the adenosine-conjugated PEG2000 nanoparticles into the affected joint completely abrogates both the development of effusion as well as the development of gross cartilage loss and histologic changes consistent with osteo-arthritis. (FIGS. 11-13). While it is likely that many of the effects of the adenosine-conjugated PEG2000 nanoparticles are mediated through direct effects on cartilage, it is also likely that some contribution is made via inhibition of inflammatory cell function.

In particular, because it was demonstrated that the adenosine-conjugated PEG2000 nanoparticles acted at adenosine A2AR and A2BR, it was next determined whether these particles could be useful in a rat post-traumatic osteoarthritis model. As shown in FIG. 11A, intra-articular injection of the adenosine-conjugated nanoparticles diminished swelling in affected knees, whereas unconjugated nanoparticles had no effect on knee swelling. More importantly, intra-articular injection of the knees with adenosine-conjugated nanoparticles prevented loss of cartilage (see the pink (lighter color) tissue in the microCT images shown in FIGS. 12A-12B, 12D-12E), as compared to the unconjugated nanoparticles (FIGS. 12A-12E).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A polymeric nanoparticle conjugate,
   wherein the nanoparticle is coupled n times to a ligand having the formula:

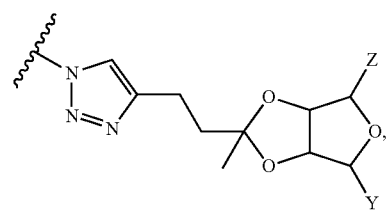

wherein

is a point of coupling the ligand to the nanoparticle;
Y is selected from the group consisting of

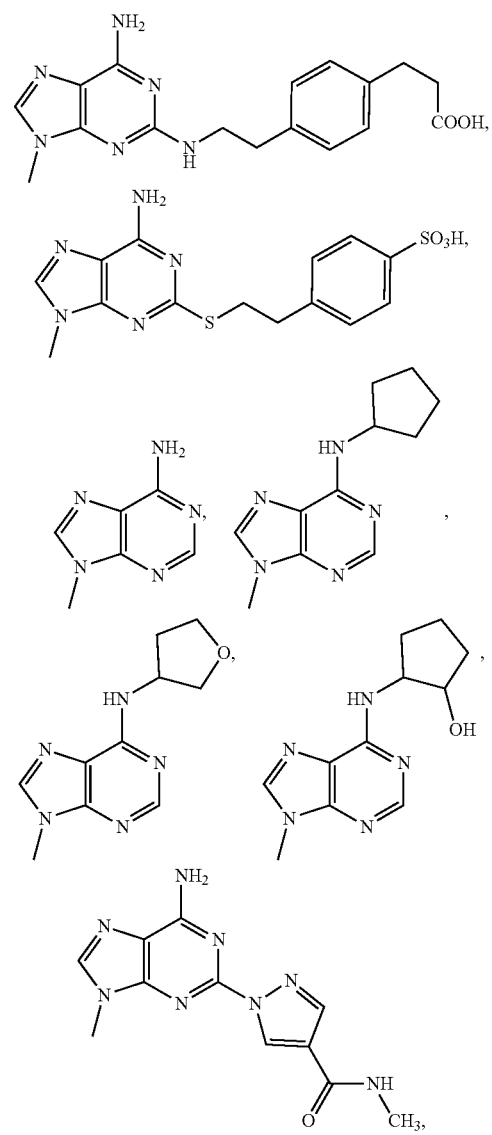

-continued

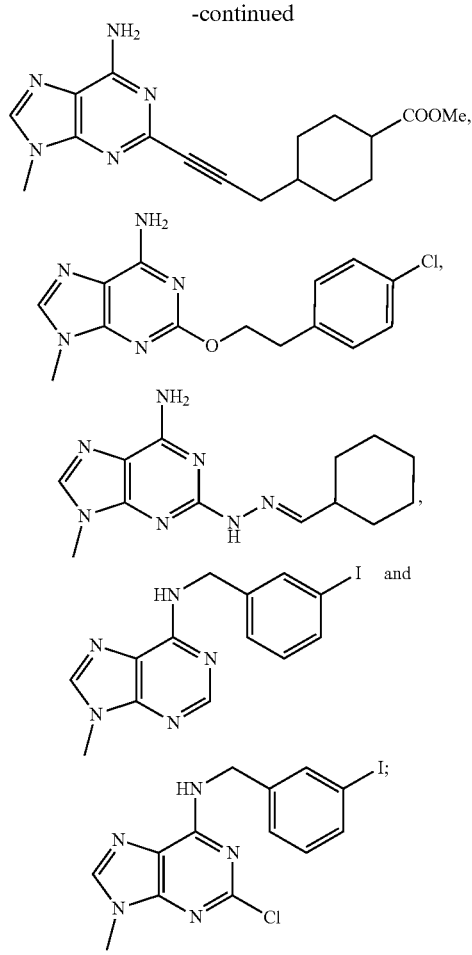

Z is selected from the group consisting of —C(O)NHEt, —C(O)NHMe, —CH₂OH, and

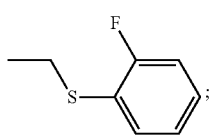

and n is 1 to 500.

2. The polymeric nanoparticle conjugate according to claim 1, wherein the nanoparticle is biodegradable.

3. The polymeric nanoparticle conjugate according to claim 1, wherein the polymeric nanoparticle is made from polyesters, poly(ester amide)s, polyurethanes, polyanhydrides, polyphosphoesters, poly(ortho esters), poly(alkyl cyanoacrylates), polyether, poly(amino acids), microbial polyesters, proteins, or polysaccharides.

4. The polymeric nanoparticle conjugate according to claim 1, wherein there is a linker group coupling the polymeric nanoparticle to the ligand, said linker being selected from the group consisting of polyethylene glycol (PEG) and polypropylene glycol (PPG).

5. A pharmaceutical composition comprising:
a pharmaceutically acceptable carrier and the polymeric nanoparticle conjugate according to claim 1.

6. A method of treating and/or preventing arthritis in a patient in need thereof comprising:
selecting a subject in need of treatment, and administering to the selected subject a therapeutically acceptable amount of a polymeric nanoparticle conjugate, wherein the nanoparticle is coupled n times to a ligand having the formula:

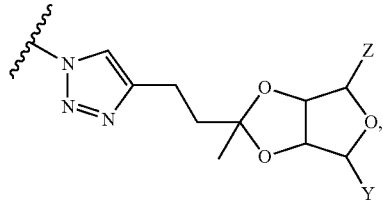

wherein

is a point of coupling the ligand to the nanoparticle,
Y is selected from the group consisting of

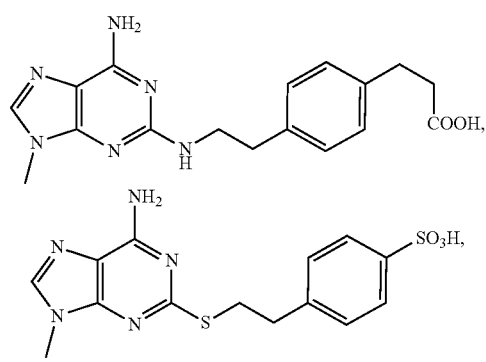

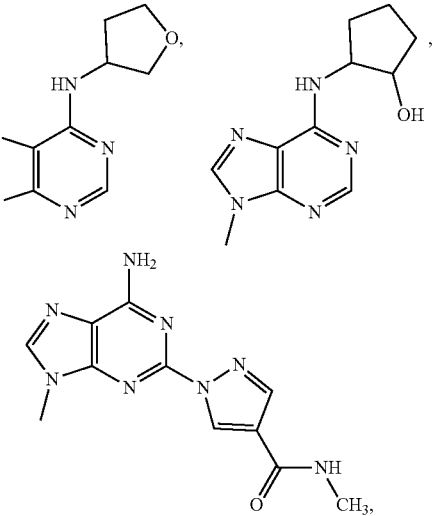

-continued

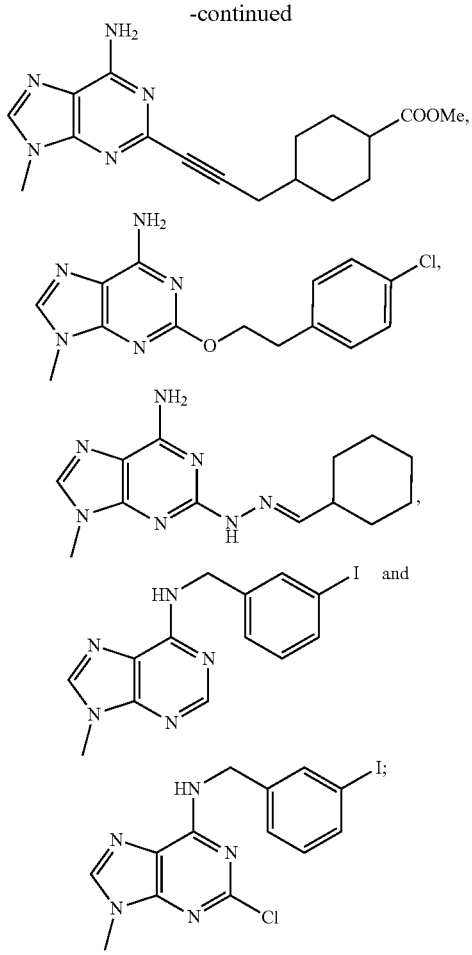

Z is selected from the group consisting of —C(O)NHEt, —C(O)NHMe, —CH₂OH, and

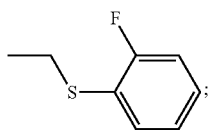

and
n is 1 to 500.

7. The method according to claim 6, wherein the polymeric nanoparticle conjugate is administered intraarticularly.

8. A method of treating a wound in a patient in need thereof comprising:
   selecting a subject in need of treatment, and
   administering to the selected subject a therapeutically acceptable amount of a polymeric nanoparticle conjugate, wherein the nanoparticle is coupled n times to a ligand having the formula:

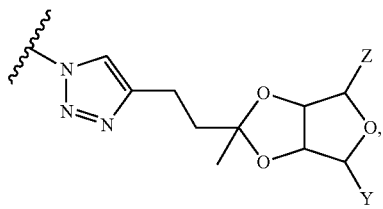

wherein

is a point of coupling the ligand to the nanoparticle;
Y is selected from the group consisting of

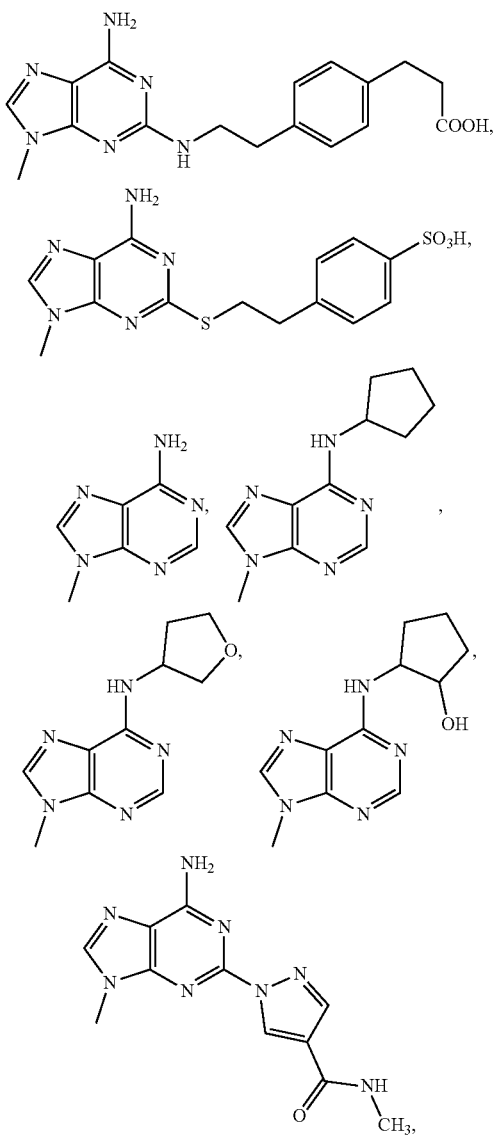

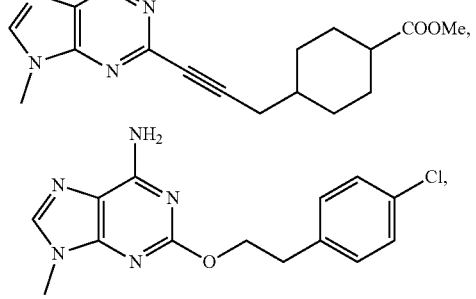

-continued

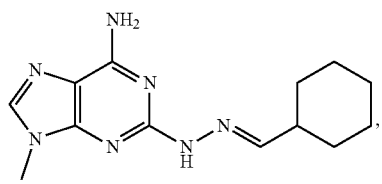

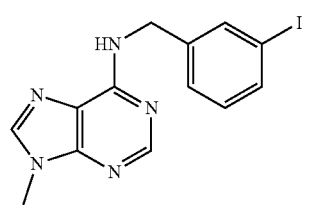
and

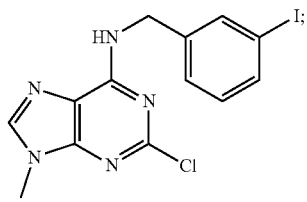

Z is selected from the group consisting of —C(O)NHEt, —C(O)NHMe, —CH₂OH, and

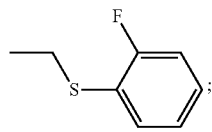

and
n is 1 to 500.

9. A method of treating a dermatological condition in a patient in need thereof comprising:
  selecting a subject in need of treatment, and
  administering to the selected subject a therapeutically acceptable amount of a polymeric nanoparticle conjugate, wherein the nanoparticle is coupled n times to a ligand having the formula:

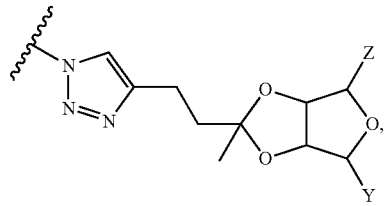

wherein

is a point of coupling the ligand to the nanoparticle;

Y is selected from the group consisting of

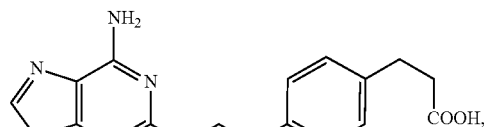

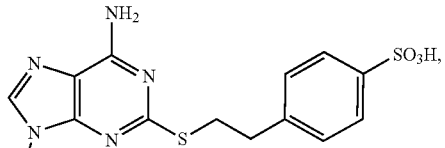

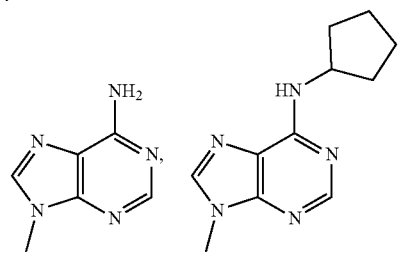

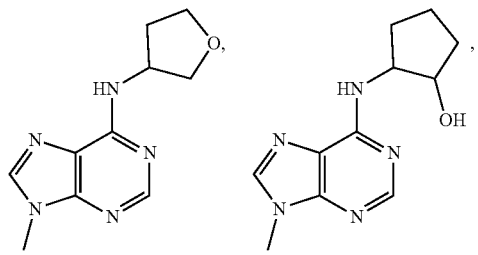

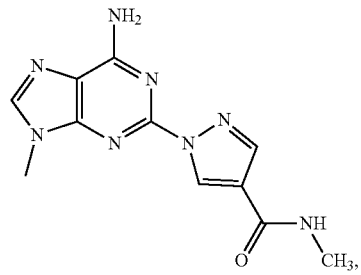

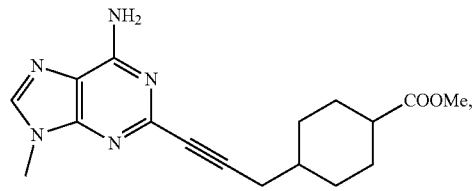

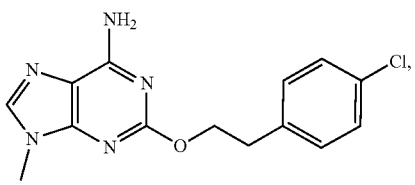

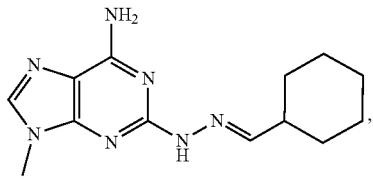

-continued

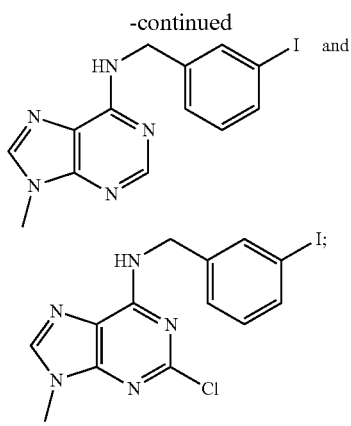

Z is selected from the group consisting of —C(O)NHEt, —C(O)NHMe, —CH₂OH, and

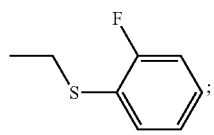

and n is 1 to 500.

10. A method of treating a joint to promote surgical healing comprising:
   selecting a subject in need of treatment, and
   administering to the selected subject a therapeutically acceptable amount of a polymeric nanoparticle conjugate, wherein the nanoparticle is coupled n times to a ligand having the formula:

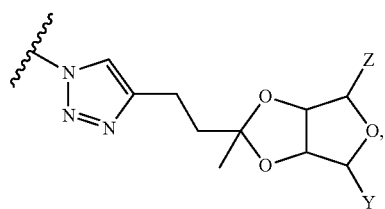

wherein

is a point of coupling the ligand to the nanoparticle;
Y is selected from the group consisting of

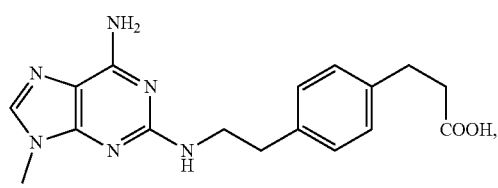

-continued

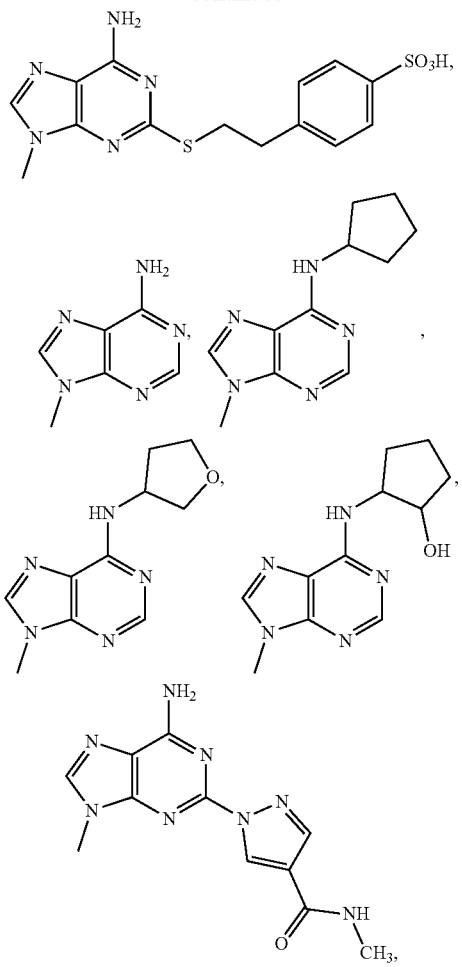

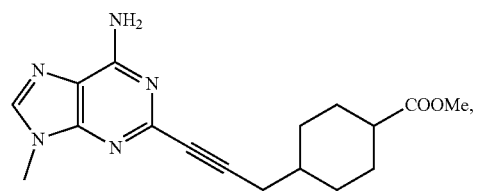

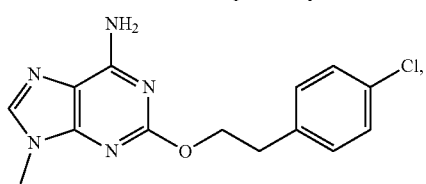

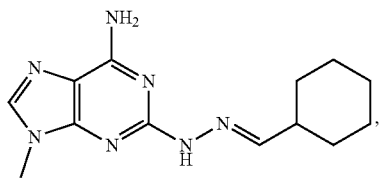

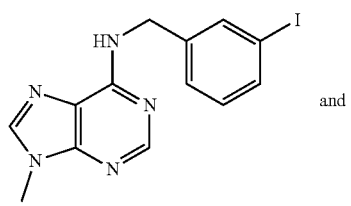

-continued

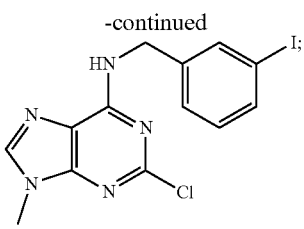

Z is selected from the group consisting of —C(O)NHEt, —C(O)NHMe, —CH₂OH, and

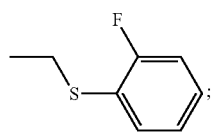

and n is 1 to 500.

11. The polymeric nanoparticle conjugate according to claim 1, wherein nanoparticle is PLA-PEG nanoparticle.

12. The polymeric nanoparticle conjugate according to claim 1, wherein the ligand has the formula:

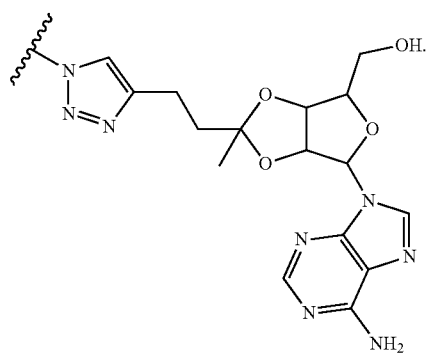 [SMILES: *n1cc(CCC2(C)OC3C(CO)OC(n4cnc5c(N)ncnc54)C3O2)nn1]

13. The polymeric nanoparticle conjugate according to claim 1, wherein Y is

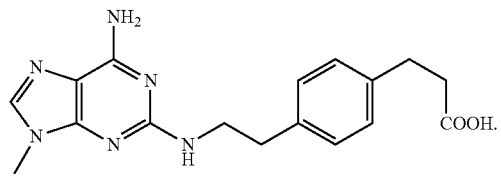 [SMILES: Cn1cnc2c(N)nc(NCCc3ccc(CCC(=O)O)cc3)nc21]

14. The polymeric nanoparticle conjugate according to claim 1, wherein Y is

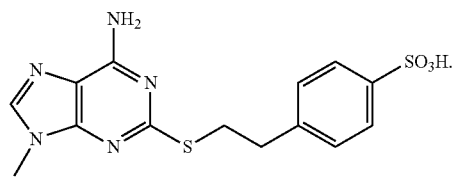 [SMILES: Cn1cnc2c(N)nc(SCCc3ccc(S(=O)(=O)O)cc3)nc21]

15. The polymeric nanoparticle conjugate according to claim 1, wherein Y is

16. The polymeric nanoparticle conjugate according to claim 1, wherein Y is

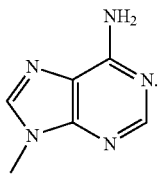

17. The polymeric nanoparticle conjugate according to claim 1, wherein Y is

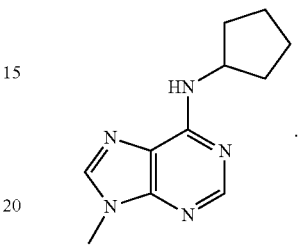

18. The polymeric nanoparticle conjugate according to claim 1, wherein Y is

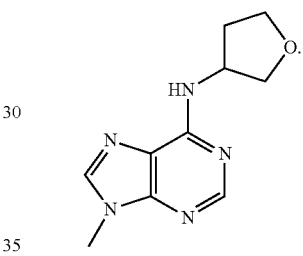

19. The polymeric nanoparticle conjugate according to claim 1, wherein Y is

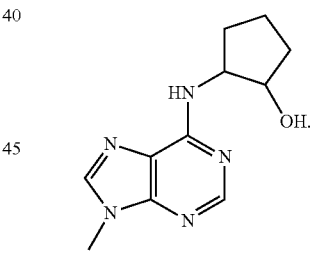

20. The polymeric nanoparticle conjugate according to claim 1, wherein Y is

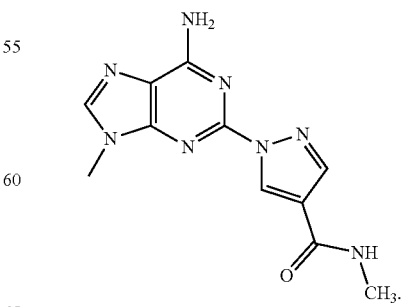

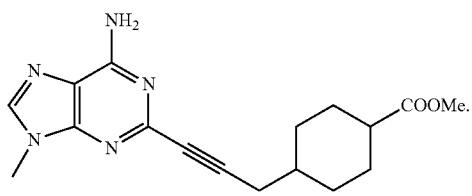 [SMILES: COC(=O)C1CCC(CC#Cc2nc(N)c3ncn(C)c3n2)CC1]

21. The polymeric nanoparticle conjugate according to claim 1, wherein Y is

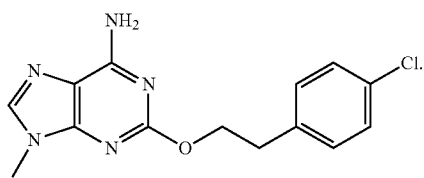 [SMILES: Cn1cnc2c(N)nc(OCCc3ccc(Cl)cc3)nc21]

22. The polymeric nanoparticle conjugate according to claim 1, wherein Y is

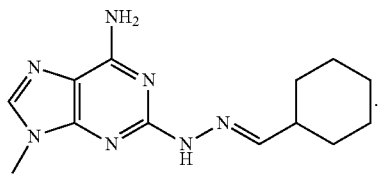 [SMILES: Cn1cnc2c(N)nc(N/N=C/C3CCCCC3)nc21]

23. The polymeric nanoparticle conjugate according to claim 1, wherein Y is

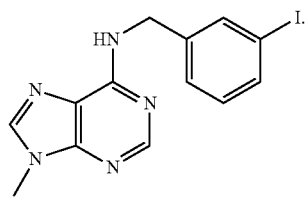 [SMILES: Cn1cnc2c(NCc3cccc(I)c3)ncnc21]

24. The polymeric nanoparticle conjugate according to claim 1, wherein Y is

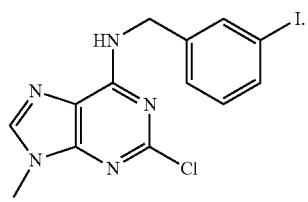 [SMILES: Cn1cnc2c(NCc3cccc(I)c3)nc(Cl)nc21]

25. The polymeric nanoparticle conjugate according to claim 1, wherein Z is —C(O)NHEt.

26. The polymeric nanoparticle conjugate according to claim 1, wherein Z is —C(O)NHMe.

27. The polymeric nanoparticle conjugate according to claim 1, wherein Z is —CH$_2$OH.

28. The polymeric nanoparticle conjugate according to claim 1, wherein Z

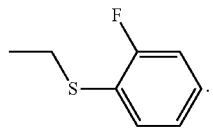

* * * * *

UNITED STATES PATENT AND TRADEMARK OFFICE
CERTIFICATE OF CORRECTION

PATENT NO.         : 10,744,209 B2
APPLICATION NO.    : 15/775575
DATED              : August 18, 2020
INVENTOR(S)        : Ulman et al.

Page 1 of 1

It is certified that error appears in the above-identified patent and that said Letters Patent is hereby corrected as shown below:

In the Specification

In Column 8, Lines 15–27, please delete the following compound:

"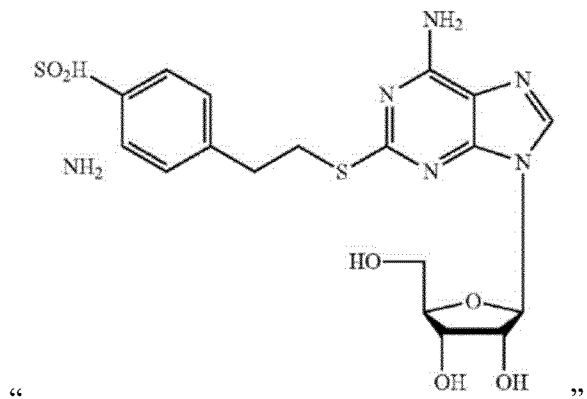"

And insert in its place the following compound:

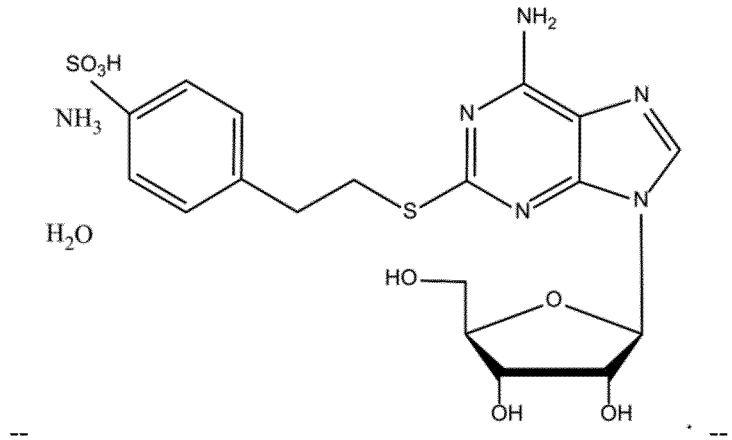 .

Signed and Sealed this
First Day of December, 2020

Andrei Iancu
*Director of the United States Patent and Trademark Office*